(12) United States Patent
Speck et al.

(10) Patent No.: US 8,257,305 B2
(45) Date of Patent: Sep. 4, 2012

(54) MEDICAL DEVICE FOR DISPENSING MEDICAMENTS

(75) Inventors: Ulrich Speck, Berlin (DE); Bruno Scheller, Saarbrücken (DE)

(73) Assignee: Bayer Pharma Aktiengesellschaft, Berlin (DE)

( * ) Notice: Subject to any disclaimer, the term of this patent is extended or adjusted under 35 U.S.C. 154(b) by 577 days.

(21) Appl. No.: 10/528,577

(22) PCT Filed: Aug. 26, 2003

(86) PCT No.: PCT/DE03/02871
§ 371 (c)(1), (2), (4) Date: Mar. 21, 2005

(87) PCT Pub. No.: WO2004/028582
PCT Pub. Date: Apr. 8, 2004

(65) Prior Publication Data
US 2006/0020243 A1    Jan. 26, 2006

(30) Foreign Application Priority Data
Sep. 20, 2002   (DE) ................................ 102 44 847

(51) Int. Cl.
*A61M 29/00* (2006.01)
(52) U.S. Cl. .................... 604/103.02; 623/1.11
(58) Field of Classification Search ............. 623/1.11; 604/103.02
See application file for complete search history.

(56) References Cited

U.S. PATENT DOCUMENTS

| | | | |
|---|---|---|---|
| 4,101,984 A | 7/1978 | MacGregor | |
| 4,217,894 A | 8/1980 | Franetzki et al. | |
| 4,247,352 A | 1/1981 | Stupp et al. | |
| 4,305,926 A | 12/1981 | Everse et al. | |
| 4,343,788 A | 8/1982 | Mustacich et al. | |
| 4,364,921 A | 12/1982 | Speck et al. | |
| 4,476,590 A | 10/1984 | Scales et al. | |
| 4,479,795 A | 10/1984 | Mustacich et al. | |
| 4,502,158 A | 3/1985 | Mouri et al. | |
| 4,502,159 A | 3/1985 | Woodroof et al. | |
| 4,532,315 A | 7/1985 | Letoffe et al. | |
| 4,573,476 A | 3/1986 | Ruiz et al. | |
| 4,677,143 A | 6/1987 | Laurin et al. | |
| 4,769,013 A | 9/1988 | Lorenz et al. | |

(Continued)

FOREIGN PATENT DOCUMENTS

CA   2 132 936 AA   3/1995

(Continued)

OTHER PUBLICATIONS

Pierre Signore et al., "Complete Inhibition of Intimal Hyperplasia by Perivascular Delivery of Paclitaxel in Balloon-injured Rat Carotid Arteries," Laboratory Investigations, vol. 12, No. 1, Jan. 2001, pp. 79-88.

(Continued)

*Primary Examiner* — Laura Bouchelle
(74) *Attorney, Agent, or Firm* — Millen, White, Zelano & Branigan, P.C.

(57) ABSTRACT

For selective treatment of diseased tissue sections or organ parts, the surface of medical devices entering into contact with areas thereof under pressure is coated with lipophilic substantially water-insoluble medicaments binding to various tissue components with good adherence thereto, said medicaments having an effect thereupon a short time after entering into contact therewith without exerting a harmful influence upon adjacent healthy tissue.

60 Claims, 1 Drawing Sheet

U.S. PATENT DOCUMENTS

| | | | |
|---|---|---|---|
| 4,776,337 A | 10/1988 | Palmaz et al. | |
| 4,793,825 A | 12/1988 | Benjamin et al. | |
| 4,872,867 A | 10/1989 | Joh | |
| 4,879,135 A | 11/1989 | Greco et al. | |
| 4,886,062 A | 12/1989 | Wiktor | |
| 4,909,799 A | 3/1990 | Thulesius et al. | |
| 4,917,686 A | 4/1990 | Bayston et al. | |
| 4,925,668 A | 5/1990 | Khan et al. | |
| 4,950,256 A | 8/1990 | Luther et al. | |
| 4,994,047 A | 2/1991 | Walker et al. | |
| 4,997,643 A | 3/1991 | Partain et al. | |
| 5,004,461 A | 4/1991 | Wilson et al. | |
| 5,019,096 A | 5/1991 | Fox, Jr. et al. | |
| 5,019,393 A | 5/1991 | Ito et al. | |
| 5,019,601 A | 5/1991 | Allen | |
| 5,051,257 A | 9/1991 | Pietronigro | |
| 5,053,048 A | 10/1991 | Pinchuk | |
| 5,059,166 A | 10/1991 | Fischell et al. | |
| 5,067,491 A | 11/1991 | Taylor et al. | |
| 5,098,977 A | 3/1992 | Frautschi et al. | |
| 5,102,402 A * | 4/1992 | Dror et al. | 604/265 |
| 5,108,424 A | 4/1992 | Hoffman et al. | |
| 5,112,457 A | 5/1992 | Marchant | |
| 5,135,516 A | 8/1992 | Sahatjian et al. | |
| 5,157,049 A | 10/1992 | Haugwitz et al. | |
| 5,163,952 A | 11/1992 | Froix | |
| 5,165,952 A | 11/1992 | Solomon et al. | |
| 5,171,217 A | 12/1992 | March et al. | |
| 5,176,626 A | 1/1993 | Soehendra et al. | |
| 5,182,317 A | 1/1993 | Winters et al. | |
| 5,197,977 A | 3/1993 | Hoffman et al. | |
| 5,217,493 A | 6/1993 | Raad et al. | |
| 5,222,971 A | 6/1993 | Willard et al. | |
| 5,229,172 A | 7/1993 | Cahalan et al. | |
| 5,232,685 A | 8/1993 | Speck et al. | |
| 5,234,456 A | 8/1993 | Silvestrin | |
| 5,244,654 A | 9/1993 | Narayanan | |
| 5,282,823 A | 2/1994 | Schwartz et al. | |
| 5,288,711 A | 2/1994 | Mitchell et al. | |
| 5,298,255 A | 3/1994 | Sawamoto et al. | |
| 5,304,121 A | 4/1994 | Sahatjian | |
| 5,306,286 A | 4/1994 | Stack et al. | |
| 5,314,688 A | 5/1994 | Kauffman et al. | |
| 5,320,634 A | 6/1994 | Vigil et al. | |
| 5,342,348 A | 8/1994 | Kaplan | |
| 5,344,411 A | 9/1994 | Domb et al. | |
| 5,344,444 A | 9/1994 | Glastra | |
| 5,345,933 A | 9/1994 | Peterson et al. | |
| 5,348,873 A | 9/1994 | Matsuda et al. | |
| 5,356,433 A | 10/1994 | Rowland et al. | |
| 5,370,614 A | 12/1994 | Amundson | |
| 5,380,299 A | 1/1995 | Fearmot et al. | |
| 5,383,927 A | 1/1995 | De Goicoechea et al. | |
| 5,383,928 A | 1/1995 | Scott et al. | |
| 5,419,760 A | 5/1995 | Narciso, Jr. | |
| 5,443,458 A | 8/1995 | Eury | |
| 5,447,724 A | 9/1995 | Helmus et al. | |
| 5,449,382 A | 9/1995 | Dayton et al. | |
| 5,454,886 A | 10/1995 | Burrell et al. | |
| 5,455,040 A | 10/1995 | Marchant | |
| 5,456,663 A | 10/1995 | Lemelson | |
| 5,457,113 A | 10/1995 | Cillinan et al. | |
| 5,464,450 A | 11/1995 | Buscemi et al. | |
| 5,464,650 A | 11/1995 | Berg et al. | |
| 5,500,013 A | 3/1996 | Buscemi et al. | |
| 5,504,102 A | 4/1996 | Agharkar et al. | |
| 5,510,330 A | 4/1996 | Martin et al. | |
| 5,531,716 A | 7/1996 | Luzio et al. | |
| 5,534,288 A | 7/1996 | Gruskin et al. | |
| 5,554,181 A | 9/1996 | Das | |
| 5,554,182 A | 9/1996 | Dinh et al. | |
| 5,559,448 A | 9/1996 | Koenig | |
| 5,567,495 A | 10/1996 | Modak et al. | |
| 5,569,463 A | 10/1996 | Helmus et al. | |
| 5,571,086 A | 11/1996 | Kaplan et al. | |
| 5,578,075 A | 11/1996 | Dayton | |
| 5,605,896 A | 2/1997 | Leonardi et al. | |
| 5,607,463 A | 3/1997 | Schwartz et al. | |
| 5,607,475 A | 3/1997 | Cahalan et al. | |
| 5,609,629 A | 3/1997 | Fearmot et al. | |
| 5,624,411 A | 4/1997 | Tuch | |
| 5,626,562 A | 5/1997 | Castro | |
| 5,629,008 A | 5/1997 | Lee | |
| 5,629,881 A | 5/1997 | Leeb et al. | |
| 5,643,580 A | 7/1997 | Subramaniam et al. | |
| 5,649,977 A | 7/1997 | Campbell et al. | |
| 5,674,192 A | 10/1997 | Sahatjian | |
| 5,679,400 A | 10/1997 | Tuch | |
| 5,681,846 A | 10/1997 | Trissel | |
| 5,693,014 A | 12/1997 | Abele et al. | |
| 5,697,967 A | 12/1997 | Dinh et al. | |
| 5,716,981 A | 2/1998 | Hunter et al. | |
| 5,733,327 A | 3/1998 | Igaki et al. | |
| 5,762,638 A | 6/1998 | Shikani et al. | |
| 5,766,158 A | 6/1998 | Opolski | |
| 5,770,198 A | 6/1998 | Coller et al. | |
| 5,772,640 A | 6/1998 | Modak et al. | |
| 5,789,018 A | 8/1998 | Engelson et al. | |
| 5,792,158 A | 8/1998 | Lary | |
| 5,814,301 A | 9/1998 | Klopp et al. | |
| 5,820,607 A | 10/1998 | Tcholakian et al. | |
| 5,824,049 A | 10/1998 | Ragheb et al. | |
| 5,827,289 A | 10/1998 | Reiley | |
| 5,837,008 A | 11/1998 | Berg et al. | |
| 5,863,745 A | 1/1999 | Fitzgerald et al. | |
| 5,873,904 A | 2/1999 | Ragheb et al. | |
| 5,886,026 A | 3/1999 | Hunter et al. | |
| 5,893,867 A | 4/1999 | Bagaoisan et al. | |
| 5,902,283 A | 5/1999 | Darouiche et al. | |
| 5,916,596 A * | 6/1999 | Desai et al. | 424/489 |
| 5,921,952 A | 7/1999 | Desmond et al. | |
| 5,922,754 A | 7/1999 | Burchett et al. | |
| 5,954,706 A | 9/1999 | Sahatjian | |
| 5,977,163 A | 11/1999 | Li et al. | |
| 5,980,972 A | 11/1999 | Ding et al. | |
| 5,981,568 A | 11/1999 | Kunz et al. | |
| 5,997,162 A | 12/1999 | English et al. | |
| 6,010,480 A | 1/2000 | Abele et al. | |
| 6,013,092 A | 1/2000 | Dehdashtian et al. | |
| 6,017,948 A | 1/2000 | Rubinfeld et al. | |
| 6,039,721 A | 3/2000 | Johnson et al. | |
| 6,071,285 A | 6/2000 | Lashinski et al. | |
| 6,096,070 A | 8/2000 | Ragheb et al. | |
| 6,123,923 A | 9/2000 | Unger et al. | |
| 6,146,358 A | 11/2000 | Rowe | |
| 6,171,232 B1 | 1/2001 | Papandreou et al. | |
| 6,177,061 B1 * | 1/2001 | Klaveness et al. | 424/9.51 |
| 6,203,487 B1 | 3/2001 | Consigny et al. | |
| 6,203,551 B1 | 3/2001 | Wu | |
| 6,207,133 B1 | 3/2001 | Reszka et al. | |
| 6,214,333 B1 | 4/2001 | Zoldhelyi et al. | |
| 6,221,467 B1 | 4/2001 | Nazarova et al. | |
| 6,231,615 B1 | 5/2001 | Preissman et al. | |
| 6,240,616 B1 | 6/2001 | Yan | |
| 6,248,100 B1 | 6/2001 | de Toledo et al. | |
| 6,064,624 A1 | 7/2001 | Desmond et al. | |
| 6,258,108 B1 | 7/2001 | Lary | |
| 6,264,624 B1 | 7/2001 | Desmond et al. | |
| 6,273,908 B1 | 8/2001 | Ndondo-Lay | |
| 6,273,913 B1 | 8/2001 | Wright et al. | |
| 6,287,285 B1 | 9/2001 | Michal et al. | |
| 6,299,604 B1 | 10/2001 | Ragheb et al. | |
| 6,306,151 B1 | 10/2001 | Lary et al. | |
| 6,306,166 B1 * | 10/2001 | Barry et al. | 623/1.46 |
| 6,335,029 B1 | 1/2002 | Kamath et al. | |
| 6,355,058 B1 | 3/2002 | Pacetti et al. | |
| 6,364,856 B1 * | 4/2002 | Ding et al. | 604/103.02 |
| 6,369,039 B1 | 4/2002 | Palasis et al. | |
| 6,369,093 B1 | 4/2002 | Elbe et al. | |
| 6,375,931 B2 | 4/2002 | Ostensen | |
| 6,406,754 B2 | 6/2002 | Chappa et al. | |
| 6,419,692 B1 | 7/2002 | Yang et al. | |
| 6,479,033 B1 | 11/2002 | Reszka et al. | |
| 6,491,619 B1 | 12/2002 | Trauthen et al. | |
| 6,491,938 B2 | 12/2002 | Kunz et al. | |
| 6,495,979 B2 | 12/2002 | Park et al. | |
| 6,500,341 B2 | 12/2002 | Wang et al. | |

| | | | | | | |
|---|---|---|---|---|---|---|
| 6,503,954 | B1 | 1/2003 | Bhat et al. | CA | 2 345 697 AA | 5/2000 |
| 6,515,016 | B2 | 2/2003 | Hunter et al. | CN | 1 224 622 A | 8/1999 |
| 6,544,223 | B1 | 4/2003 | Kokish et al. | DE | 4225553 | 5/1994 |
| 6,544,544 | B2 | 4/2003 | Hunter et al. | DE | 4225553 C1 | 5/1994 |
| 6,562,024 | B2 | 5/2003 | Alvarez de Toledo et al. | DE | 4446694 | 12/1994 |
| 6,575,888 | B2 | 6/2003 | Zamora et al. | DE | 4334272 | 4/1995 |
| 6,585,765 | B1 | 7/2003 | Hossainy et al. | DE | 4341478 A1 | 6/1995 |
| 6,599,275 | B1 | 7/2003 | Fischer et al. | DE | 44 35 652 | 4/1996 |
| 6,599,448 | B1 | 7/2003 | Ehrhard et al. | DE | 195 14 104 | 11/1996 |
| 6,599,928 | B2 | 7/2003 | Kunz et al. | DE | 69119753 | 1/1997 |
| 6,616,591 | B1 | 9/2003 | Teoh et al. | DE | 69403966 | 2/1998 |
| 6,616,650 | B1 | 9/2003 | Rowe | DE | 19724796 A1 | 12/1998 |
| 6,635,082 | B1 | 10/2003 | Hossainy et al. | DE | 69925936 | 6/2000 |
| 6,638,913 | B1 | 10/2003 | Speck et al. | DE | 10115740 | 10/2002 |
| 6,656,156 | B2 | 12/2003 | Yang et al. | DE | 10244847.7 | 11/2002 |
| 6,682,545 | B1 | 1/2004 | Kester et al. | DE | 69925936 | 7/2005 |
| 6,682,546 | B2 | 1/2004 | Amplatz | DE | 20122736 | 8/2007 |
| 6,695,811 | B2 | 2/2004 | Samson et al. | EP | 1 118 325 B1 | 11/1986 |
| 6,706,892 | B1 | 3/2004 | Ezrin et al. | EP | 0357003 | 3/1990 |
| 6,730,064 | B2 | 5/2004 | Ragheb et al. | EP | 0470246 | 2/1992 |
| 6,774,278 | B1 | 8/2004 | Ragheb et al. | EP | 0 551 182 | 7/1993 |
| 6,867,190 | B2 | 3/2005 | Carney et al. | EP | 0706376 | 7/1993 |
| 6,918,927 | B2 | 7/2005 | Bates et al. | EP | 0578998 | 1/1994 |
| 7,060,051 | B2 | 6/2006 | Palasis et al. | EP | 0604022 | 6/1994 |
| 7,179,251 | B2 | 2/2007 | Palasis | EP | 0623354 | 11/1994 |
| 7,419,683 | B2 | 9/2008 | Szebeni et al. | EP | 673114 | 9/1995 |
| 7,445,792 | B2 | 11/2008 | Toner et al. | EP | 0681475 | 11/1995 |
| 7,491,234 | B2 | 2/2009 | Palasis et al. | EP | 0706376 A1 | 4/1996 |
| 7,611,532 | B2 | 11/2009 | Bates et al. | EP | 0717041 | 6/1996 |
| 7,731,685 | B2 | 6/2010 | Bates et al. | EP | 0747069 | 12/1996 |
| 7,750,041 | B2 | 7/2010 | Speck et al. | EP | 0797988 | 10/1997 |
| 7,811,622 | B2 | 10/2010 | Bates et al. | EP | 0975340 | 2/2000 |
| 2001/0014717 | A1 | 8/2001 | Hossainy et al. | EP | 0 551 182 B1 | 7/2000 |
| 2001/0034363 | A1 | 10/2001 | Li et al. | EP | 0829238 B1 | 9/2000 |
| 2001/0037140 | A1 | 11/2001 | Gaudoin et al. | EP | 1037605 | 9/2000 |
| 2001/0044651 | A1 | 11/2001 | Steinke et al. | EP | 1090637 | 4/2001 |
| 2002/0013549 | A1 | 1/2002 | Zhong et al. | EP | 1140273 B1 | 10/2001 |
| 2002/0032414 | A1 | 3/2002 | Ragheb et al. | EP | 1 669 092 | 12/2001 |
| 2002/0037358 | A1 | 3/2002 | Barry et al. | EP | 1250166 | 10/2002 |
| 2002/0098278 | A1 | 7/2002 | Bates et al. | EP | 1407786 | 4/2004 |
| 2002/0123505 | A1 | 9/2002 | Burke et al. | EP | 1447098 | 8/2004 |
| 2002/0193828 | A1 | 12/2002 | Griffin et al. | EP | 1512398 | 3/2005 |
| 2003/0007944 | A1 | 1/2003 | O'Halloran et al. | EP | 1521603 | 4/2005 |
| 2003/0028243 | A1 | 2/2003 | Bates et al. | EP | 1536850 | 6/2005 |
| 2003/0028244 | A1 | 2/2003 | Bates et al. | EP | 1159974 | 12/2005 |
| 2003/0036794 | A1 | 2/2003 | Ragheb et al. | EP | 1 666 071 A1 | 6/2006 |
| 2003/0059454 | A1 | 3/2003 | Barry et al. | EP | 1666070 | 6/2006 |
| 2003/0100600 | A1 | 5/2003 | Kinsella et al. | EP | 1669091 | 6/2006 |
| 2003/0195548 | A1 | 10/2003 | Kester | EP | 1 372 737 B1 | 8/2006 |
| 2004/0068241 | A1 | 4/2004 | Fischer | EP | 1695697 | 8/2006 |
| 2004/0073284 | A1* | 4/2004 | Bates et al. ............ 623/1.11 | EP | 1695698 | 8/2006 |
| 2004/0115228 | A1 | 6/2004 | Costa et al. | EP | 1735042 | 12/2006 |
| 2004/0224003 | A1* | 11/2004 | Schultz ............ 424/423 | EP | 1781209 | 5/2007 |
| 2004/0243225 | A1 | 12/2004 | Ragheb et al. | EP | 2092941 | 8/2009 |
| 2005/0042295 | A1 | 2/2005 | Hunter et al. | EP | 2092942 | 8/2009 |
| 2005/0063926 | A1 | 3/2005 | Bathina et al. | EP | 2098230 | 9/2009 |
| 2005/0101522 | A1 | 5/2005 | Speck et al. | JP | 06-63145 | 3/1994 |
| 2005/0123605 | A1 | 6/2005 | Hunter et al. | JP | 6 63145 | 3/1994 |
| 2005/0222677 | A1 | 10/2005 | Bates et al. | JP | 06-063145 | 3/1994 |
| 2005/0250672 | A9 | 11/2005 | Speck et al. | JP | 7500585 | 1/1995 |
| 2005/0278021 | A1 | 12/2005 | Bates et al. | JP | 7-328124 | 12/1995 |
| 2006/0020243 | A1 | 1/2006 | Speck et al. | JP | 07-328124 | 12/1995 |
| 2006/0020331 | A1 | 1/2006 | Bates et al. | JP | 7 328124 | 12/1995 |
| 2007/0128118 | A1 | 6/2007 | Yu et al. | JP | 10 509691 | 9/1998 |
| 2008/0012034 | A1 | 1/2008 | Thielen et al. | JP | 10509691 | 9/1998 |
| 2008/0102033 | A1 | 5/2008 | Speck et al. | JP | 11012160 A | 1/1999 |
| 2008/0102034 | A1 | 5/2008 | Speck et al. | JP | 2000 507930 | 6/2000 |
| 2008/0118544 | A1 | 5/2008 | Wang | JP | 2000507930 | 6/2000 |
| 2008/1012034 | | 5/2008 | Speck et al. | JP | 2001 508320 | 6/2001 |
| 2008/0175887 | A1 | 7/2008 | Wang | JP | 2002 536058 | 10/2002 |
| 2008/0255508 | A1 | 10/2008 | Wang | JP | 36371777 | 3/2005 |
| 2008/0255509 | A1 | 10/2008 | Wang | WO | WO-90/13293 | 11/1990 |
| 2008/0255510 | A1 | 10/2008 | Wang | WO | WO-90/13332 | 11/1990 |
| | | | | WO | WO-91/12779 | 9/1991 |
| | FOREIGN PATENT DOCUMENTS | | | WO | WO 92/11890 A1 | 7/1992 |
| CA | 2 207 025 | | 6/1996 | WO | WO-92/11896 | 7/1992 |
| CA | 2207025 AA | | 6/1996 | WO | WO 9211890 | 7/1992 |
| CA | 2 218 103 | | 10/1996 | WO | WO-92/12717 | 8/1992 |
| CA | 2 345 729 AA | | 4/2000 | WO | WO 92/15282 | 9/1992 |

| | | |
|---|---|---|
| WO | WO 9215282 | 9/1992 |
| WO | WO 92/20718 A2 | 11/1992 |
| WO | WO-93/06792 | 4/1993 |
| WO | WO 93/07875 | 4/1993 |
| WO | WO-93/09762 | 5/1993 |
| WO | WO-93/09765 | 5/1993 |
| WO | WO-93/11120 | 6/1993 |
| WO | WO-93/11668 | 6/1993 |
| WO | WO 00/50105 A2 | 2/1994 |
| WO | WO 94/07484 | 4/1994 |
| WO | WO-94/07529 | 4/1994 |
| WO | WO-94/16706 | 8/1994 |
| WO | WO 94/23787 A1 | 10/1994 |
| WO | WO-94/25020 | 11/1994 |
| WO | WO-94/26291 | 11/1994 |
| WO | WO 95/03036 A1 | 2/1995 |
| WO | WO 95/03083 | 2/1995 |
| WO | WO 95/03795 | 2/1995 |
| WO | WO 95/15782 A1 | 6/1995 |
| WO | WO 96/17629 | 6/1996 |
| WO | WO-96 39949 | 6/1996 |
| WO | WO 96/20718 | 7/1996 |
| WO | WO 96/25176 | 8/1996 |
| WO | WO 96/25282 | 8/1996 |
| WO | WO 96/38183 | 12/1996 |
| WO | WO 96/39949 A1 | 12/1996 |
| WO | WO 96/39970 A1 | 12/1996 |
| WO | WO-97/01327 | 1/1997 |
| WO | WO 97/26862 | 1/1997 |
| WO | WO 97/17098 A1 | 5/1997 |
| WO | WO-97/31674 | 9/1997 |
| WO | WO 97/33552 | 9/1997 |
| WO | WO-97/33552 | 9/1997 |
| WO | WO-97 33552 | 9/1997 |
| WO | WO-97/41916 | 11/1997 |
| WO | WO 98/11933 A1 | 3/1998 |
| WO | WO 98/14174 | 4/1998 |
| WO | WO 98/15282 A1 | 4/1998 |
| WO | WO 98/24427 | 6/1998 |
| WO | WO 98/25176 A1 | 6/1998 |
| WO | WO 98/30249 | 7/1998 |
| WO | WO-98 31415 | 7/1998 |
| WO | WO 0006152 | 7/1998 |
| WO | WO 98/36784 | 8/1998 |
| WO | WO-99 08729 | 8/1998 |
| WO | WO-98/43618 | 10/1998 |
| WO | WO 98/47540 A1 | 10/1998 |
| WO | WO 9843618 | 10/1998 |
| WO | WO-99/08729 | 2/1999 |
| WO | WO-99/09729 | 2/1999 |
| WO | WO 99/12577 A1 | 3/1999 |
| WO | WO 99/13916 A2 | 3/1999 |
| WO | WO 99/19004 A2 | 4/1999 |
| WO | WO-99 25336 | 5/1999 |
| WO | WO-99/30684 | 6/1999 |
| WO | WO-00 21584 | 10/1999 |
| WO | WO 99/55396 | 11/1999 |
| WO | WO-99/59556 | 11/1999 |
| WO | WO 99/62510 | 12/1999 |
| WO | WO-00/00023 | 1/2000 |
| WO | WO-00/00238 | 1/2000 |
| WO | WO-00 45744 | 1/2000 |
| WO | WO 00/10552 | 3/2000 |
| WO | WO 00/21584 A1 | 4/2000 |
| WO | WO-00 32238 | 6/2000 |
| WO | WO 00/32238 A1 | 6/2000 |
| WO | WO-00 32267 | 6/2000 |
| WO | WO 00/32267 | 6/2000 |
| WO | WO 00/44414 A1 | 8/2000 |
| WO | WO 00/45744 | 8/2000 |
| WO | WO-00 45744 | 8/2000 |
| WO | WO-00/47197 | 8/2000 |
| WO | WO 0044414 | 8/2000 |
| WO | WO 0045744 | 8/2000 |
| WO | WO-01/24866 | 4/2001 |
| WO | WO 01/24866 A1 | 4/2001 |
| WO | WO 01/49338 A1 | 7/2001 |
| WO | WO-01/54748 | 8/2001 |
| WO | WO-01 76525 | 10/2001 |
| WO | WO 01/83016 A2 | 11/2001 |
| WO | WO 02066092 | 8/2002 |
| WO | WO-02 076509 A2 | 10/2002 |
| WO | WO-02 076509 A2 | 10/2002 |
| WO | WO 02/076509 A2 | 10/2002 |
| WO | WO-03 022264 | 3/2003 |
| WO | WO 03/026718 A1 | 4/2003 |
| WO | WO-03/41686 | 5/2003 |
| WO | WO 03/048166 | 6/2003 |
| WO | WO2004/006976 | 1/2004 |
| WO | WO-2004/022124 | 3/2004 |
| WO | WO 2004/028582 | 4/2004 |
| WO | WO 2004/028610 A2 | 4/2004 |
| WO | WO-2005/089855 | 9/2005 |
| WO | WO-2005 112570 | 12/2005 |
| WO | WO-2006/023104 | 3/2006 |
| WO | WO-2008/063576 | 5/2008 |
| WO | WO-2009/051614 | 4/2009 |
| WO | WO-2009/051615 | 4/2009 |
| WO | WO-2009/051616 | 4/2009 |
| WO | WO-2009/051618 | 4/2009 |

OTHER PUBLICATIONS

File History of U.S. Appl. No. 60/395,434, filed Jul. 12, 2002.
File History of U.S. Appl. No. 60,244,446, filed Oct. 31, 2000.
Ran Kornowski et al., "Slow-Release Taxol Coated GRIT™ Stents Reduce Neointima Formation in a Porcine Coronary In-Stent Restenosis Model," 70th Scientific Sessions of the American Heart Association, Nov. 9-12, 1997.
Alan W. Heldman et al., "Paclitaxel Stent Coating Inhibits Neointinal Hyperplasia at 4 Weeks in a Porcine Model of Coronary Restenosis," Circulation, May 8, 2001, pp. 2289-2295.
Department of Health and Human Services Notice of Intramural Research Project, Oct. 1, 1993-Sep. 30, 1994; "Molecular Strategies to Treat Restenosis," 4 pp.
Department of Health and Human Services Notice of Intramural Research Project, Oct. 1, 1994-Sep. 30, 1995, "Local Delivery of Therapeutic Agents for the Prevention of Restenosis," 6 pp.
Teruo Inoue et al., "Comparison of Activation Process of Platelets and Neutrophils After Coronary Stent Implantation Versus Balloon Angioplasty for Stable Angina Pectoris," The American Journal of Cardiology, vol. 86, Nov. 15, 2000, pp. 1057-1062.
Eric K. Rowinsky et al., "Paclitaxel (Taxol)", Alastair JJ. Wood, ed. "Drug Therapy," The New England Journal of Medicine, vol. 332, No. 15, Apr. 13, 1995, pp. 1004-1014.
Dorothea I. Axel et al., "Paclitaxel Inhibits Arterial Smooth Muscle Cell Proliferation and Migration in Vitro and in Vivo Using Local Drug Delivery," Circulation, 1997, vol. 96, pp. 636-645.
Bruno Scheller et al., "Acute Cardiac Tolerance of Current Contrast Media and the New Taxane Protaxel Using Iopromide as Carrier During Porcine Coronary Angiography and Stenting," Investigative Radiology, vol. 37, No. 1, pp. 29-34.
Martin Oberhoff et al., "Local delivery of Paclitaxel using the double-ballon perfusion catheter before stenting in the porcine coronary artery," 2001,Catheterization and Cardiovascular Interventions, pp. 562-568, vol. 53.
Christopher J. Creel et al., "Arterial Paclitaxel distribution and deposition," Circulation Research, Apr. 28, 2000, pp. 879-884.
Dr. Karsch, "Lokale Applikation von Paclitaxel mit dem Schneider-Doppelballon," nach experimenteller Stentimplantation an den Koronararterien des Schweines, Gießen 2001.
Toru Kataoka et al., "7-Hexanoyltaxol-Eluting Stent for prevention of Neointimal Growth," Circulation, Oct. 1, 2002, pp. 1788-1793.
Roger Charles et al., "Ceramide-coated balloon catheters limit neointimal hyperplasia after stretch injury in carotid arteries," Circulation Research, Aug. 18, 2000, pp. 282-288.
Elsevier Science Publishers, Amsterdam, NL; Jackson D.M. A. et al Current usage of contrast agents, anticoagulant and antiplatelet drugs in angiography and angioplasty in the UK. retrieved from STN Database accession No. 95327068 XP002226116.
International Preliminary Examination Report for PCT/DE2003/002871.
International Preliminary Examination Report for PCT/DE2001/04782.

Nishio, K., et al., "Enhanced Interaction Between Tubulin and Microtubule-Associated Protein 2 Via Inhibition of Map Kinase and CDC2 Kinase by Paclitaxel," Int. J. Cancer: 63, 688-693 (1995).
Ding, A., et al., "Association of Mitogen-Activated Protein Kinases with Microtubules in Mouse Macrophages," J. Exp. Med., vol. 183, Apr. 1996, 1899-1904.
Lieu, C.-H., et al., "Role of Mitogen-Activated Protein Kinase in Taxol-Induced Apoptosis in Human Leukemic U937 Cells[1]," Cell Growth & Differentiation, vol. 9, pp. 767-776, Sep. 1998.
Japanese Final Rejection in Co-pending Application No. JP2004-538964 dated Mar. 9, 2010.
Opposition to corresponding EP1539266 by Boston Scientific Ltd., Mar. 10, 2010.
Liggins, Richard T. et al., "Paclitaxel loaded poly(L-lactic acid) microspheres: properties of microspheres made with low molecular weight polymers," International Journal of Pharmaceutics, 2001, vol. 222, pp. 19-33.
Dordunoo, S. K. et al., "Release of taxol from poly($\epsilon$-caprolactone) pastes: effect of water-soluble additives," Jounral of Controlled Release, 1997, vol. 44, pp. 87-94.
Wichert, B et al., "Low Molecular weight PLA: a suitable polymer for pulmonary administered microparticles?" J. Microencapsulation, 1993, vol. 10, No. 2, pp. 195-207.
Nairn, John A., "Polymer Characterization," Materials Science & Engineering 5473, 2003, Ch. 3, pp. 43-55.
Cremers et al., "V1742—Paclitaxel-beschictete PTCA-Katheter: Gibt es Unterschiede? Einfluss von PACCOCATH and DIOR Ballonkathetern auf die Neointimaporliferation an Schweinekoronarien," Clin. Res. Cardiol., 1997.
Cremers, B et al., "Comparison of two different paclitaxel-coated balloon catheters in the porcine coronary restenosis model," Clin. Res. Cardiol., 2009, vol. 98, pp. 325-330.
Grossmann, S, "Neuartige Zubereitungen Hemmung der Neointimaproliferation in verengten Arterien," Dissertation zur Erlangung des akademischen Grades des Doktors der Naturwissenschaften (Dr. rer. nat.), Nov. 2006.
Sollott, Steven J. et al., "Taxol Inhibits Neointimal Smooth Muscle Cell accumulation after angioplasty in the rat," The Journal of clinical Investigation, Apr. 1995, vol. 95, pp. 1869-1876.
BC, "Lippold in Retardarzneiformen" in E. Nurnberg, Hagers Handbuch der pharmazeutischen Praxis, vol. 2, Springer-Verlag Berlin Heidelburg New York, 5$^{th}$ edition, 1991, pp. 832-840.
Langer, R., "New methods of drug delivery," Science, Sep. 28, 1990, vol. 249, pp. 1527-1533.
Kirk-Othmer, Encyclopedia of Chemical Technology, 3$^{RD}$ Edition, vol. 17, 1982, John Wiley & Sons, pp. 281-310.
Voigt, R., Lehrbuch der pharmazeutishchen Technologie, 5$^{th}$ edition, VEB Verlag Volk und Gesundheit Berlin, 1984, p. 689.
Tawashi, R. "The dissolution rates of crystalline drugs," J. Mond. Pharm. 1968, vol. 4, No. 11, pp. 371-379.
Coomber and Gotlieb, Arteriosclerosis, 1990, vol. 10, No. 2, pp. 215-222.
Bartoli et al., J. Microencapulation, 1990, vol. 7, No. 2, pp. 191-197.
Garcia-Matinez et al., "Effects of taxol on endothelial cells of the developing semilunar heart valves in the chick embryo," Acta Anat, 1988, vol. 133, pp. 282-288.
Muller et al., JACC, 1990, vol. 17, No. 6, pp. 126B-131B.
Slepian, in textbook of interventional cardiology, 1990, Section IV, Chapter 32, pp. 647-670.
Single e-mail from SIGMA Chemical Company of Feb. 15, 2007 to Dr. Sollot confirming that from 1991—1993 the material was listed in their catalog as "Taxol," and that the name was changed in their catalog from "taxol" to "paclitaxel" in 1994.
Hiatt et al., "Drug-eluting stents for the prevention of restenosis: in quest for the Holy Grail,"Catheterization and Cardiovascular Interventions, 2002, vol. 55, pp. 409-417.
Forth, W. et al. "Allegemeine und spezielle Pharmakologie und Toxikologie," 7 Auflage. Heidelberg: Spektrum Akademischer Verlag, 1996, Chapter, 1, 2, 3.
Liggins, R. T. et al., J. Pharma. Sci., 1997, vol. 86, pp. 1458-1463.
Matthew, R. T. et al., J. Med. Chem., 1992, vol. 35, pp. 141-151.
Tarr, B. D. et al., J. Parent Sci. Technol., 1987, vol. 41, pp. 31-33.
Swindell, C.S. et al., J. Med. Chem, 1991, vol. 34, pp. 1176-1184.
Sharma, U. S. et al., J. Pharma. Sci., 1995, vol. 84, pp. 1223-1230.
Barath et al., JACC, 1989, vol. 13, No. 4, pp. 252A.
Cox et al., Coronary Artery Disease, 1992, vol. 3, pp. 237-248.
Voisard et al., Coronary Artery Disease, 1993, vol. 4, pp. 935-942.
Untersuchungen in vitro and in vivo, Zeitschrift fur kardiologie, Band 89, Heft 5, 2000, pp. 390-397.
Printout from the website of Bayer HealthCare Pharmaceuticals, indicating that Ultravist has been commercially available since 1985.
Mitchel et al., Circulation, Oct. 1994, vol. 90, pp. 1979-1988.
Kandarpa et al., J. Vasc. Inter. Radiol., Nov./ Dec. 1997, vol. 8, pp. 997-1004.
Kandarpa et al., J. Vasc. Inter. Radiol., May/ Jun. 1998, vol. 9, pp. 487-493.
Baron et al., Cardiovascular Research, Jun. 2000, vol. 46, pp. 585-594.
Office Action issued by the European Patent Office on Sep. 15, 2005.
Claims enclosed with Office Action issued by European Patent Office on Sep. 15, 2005.
Response filed on Jan. 13, 2006.
The decision to revoke EP1140273 B1 (=D11EP) of Oct. 23, 2007.
Clincal Cardiology Divergent Effects on Coronary Artery Disease: Abstract from 70$^{th}$ Scientific Session: Circulation, vol. 96, No. 8, Oct. 21, 2007.
Khan, I et al., Drug Development and Industrial Pharmacy, 2005, vol. 31, pp. 59-78.
Buaayk KK, "Balloon Catheter for Intravascular Dosing," Patent Abstracts of Japan, Publication Date: Mar. 8, 1994, English Abstract of JP06-063145.
Terumo Corp, "Medicine dosing catheter," Patent Abstracts of Japan, Publication Date: Dec. 19, 1995, English Abstract of JP07-328124.
International Program on Chemical Safety, General Chemical Information Chart.
Speck, Ulrich—German Priority Document for file No. 101 15 740.1 filed on Mar. 26, 2001.
Parker, Sybil P., "Micelle," McGraw-Hill Encyclopedia of Chemistry—Second Edition, 1992, pp. 638-639.
Sangster, J. et al., Octanol-Water Partition Coefficients: Fundamentals and Physical Chemistry, 1997, vol. 2 of Wiley Series in Solution Chemistry, pp. 1-49.
Online Extract From SIGMA-Aldrich Web Site Concerning Poly Vinyl Alcohol (Molecular Weight: MW 500) 2008.
Online Extract From SIGMA-Aldrich Web Site Concerning Poly Vinyl Alcohol (Molecular Weight: MS 1700) 2008.
Online Extract From MSDS Online Concerning Sucrose 2007.
Online Extract From Polysciences, Inc. Web Site Concerning Poly Lactic Acid (Molecular Weight: MW 1600 to 2400) 2008.
Online Extract From Polysciences, Inc Web Site Concerning Polyvinylpyrrolidone (Molecular Weight: MW 2500) 2008.
Online Extract From Polysciences, Inc. Web Site Concerning Polycaprolactone (Molecular Weight: MW 2000) 2008.
Online Extract From Polysciences, Inc Web Site Concerning Polycaprolactone (Molecular Weight: MW: 1250) 2008.
Online Extract From SIGMA-Alrich Web Site Concerning Poly Actylic Acid (Molecula Weight: MW 1800) 2008.
Schwartz et al.: "Preclinical Restenosis Models and Drug-Eluting Stents", Journal of the American College of Cardiology, 2004, vol. 44, No. 7, p. 1373-1385, Elsevier Inc.
Badapulle et al.: "A Hierarchical Bayesian Meta-Analysis of Randomised Clinical Trials of Drug-Eluting Stents", Lancet, 2004, vol. 364, pp. 583-591.
Scheller et al.: "Treatment of Coronary In-Stent Restenosis With a Paclitaxel-Coated Balloon Catheter", The New England Journal of Medicine, 2006, vol. 355, No. 20, pp. 2113-2124.
Licha et al.: "Hydrophilic Cyanine Dyes As Contrast Agents for Near-Infrared Tumor Imaging: Synthesis, Photophysical Properties and Spectroscopic in Vivo Characterization", Phtochemistry and Photobiology, 2000, vol. 72, No. 3, pp. 392-398.
Phillips et al.: "A-Level Biology", Oxford University Press, 1989, pp. 7-8.
Pschyrembel Klinisches Worterbuch -German Clinical Dictionary and Reference Book by Walter de Gruyter GmbH & Co. KG 1997, p. 717 (Hyperplasia).
"Stent", www.thefreedictionary.com/stent, 2000.

"The Definition of Coated Stent", www.medterms.com. 2003.
"Balloon Catheter", en.wikipedia.org/wiki/balloon_catheter, 2008.
Singla, Ak et al.: "Paclitaxel and Its Formulations", Int, J. Pharmaceutics 235 (2002): 179-192.
Nuijen, B.et al.: "Progress in the Development of Alternative . . ." Investigational New Drugs, 19 (2001): 143-153.
Speck et al., Inhibition of Restenosis in Stented Procine Coronay . . . , Invest. Radiol. 2004, 39, 182-186.
Heartwire, Jan. 22, 2003: Drugeluting Stents: Where Are They Now; p. 2, Communication of www.theheart.org.
Scheller et al., Addition of Paclitaxel to Contrast Media Prevents Restenosis After Coronary Stent Implanation, J. Am. Coll. Radiol. 2003: 42:1415-1420.
Scheller et al., Pactlitaxel Balloon Coating—A Novel Method for Prevention and Therepy of Restenosis; Circulation 2004; 110:810-814.
Li et al., J. Nucl. Med., 38 (7), 1042-47 (1997).
Perflorocarbon Compounds As X-Ray Contrast Media in the Lungs Bulletin Soc, Int. Chic. 1975, 34 (2) 137-41.
Paclitaxel: Ein Chemotherapeuticum Zur Restenoseprohylaze? Experimentelle Untersuchengen in Vitro Und in Cico, Zeitschrift Fur Kardiologie, Band 89, HEFT 5 (2000), pp. 390-397.
Herdeg et al., J. Am. Coll. Cardiol. 35 1969-1976.
Engelmann et al, 2007 International Journal of Pharmaceutics 329, 12-18.
Print-out from an online tool for calculating a coefficient of distribution between octanol and water.
Werk et al., "Inhibition of Restenosis in Femoropopliteal Arteries; Paclitaxel-Coated Bersus Uncaoted Calloon ; Femoral Paclitaxel Randomized Pilot Trial", Circulation: Journal of the American Heart Association, 2008, vol. 118, pp. 1358.
Tepe et al., "Local Delivery of Paclitaxel to Inhibit Restenosis During Angioplasty of the Leg", The New England Journal of Medicine, 2008, vol. 358, No. 7, pp. 689-699.
Henry et al., "'POBA Plus' : Will the Balloon Regain Its Luster ?", Circulation: Journal of the American Heart Association, 2008, vol. 118, pp. 1309-1311.
Final Rejection dated May 1, 2008 in related U.S. Appl. No. 10/528,577, filed Mar. 21, 2005.
Non-Final Rejection dated Jul. 2, 2007 in related U.S. Appl. No. 10/472,844, filed Sep. 26, 2003.
Final Rejection dated Nov. 1, 2007 in related U.S. Appl. No. 10/472,844, filed Sep. 26, 2003.
Non-Final Rejection dated May 29, 2008 in related U.S. Appl. No. 10/472,844, filed Sep. 26, 2003.
Final Rejection dated Mar. 4, 2009 in related U.S. Appl. No. 10/472,844, filed Sep. 26, 2003.
Non-Final Rejection dated Jan. 15, 2009 in related U.S. Appl. No. 10/618,977, filed Jul. 14, 2003.
Non-Final Rejection dated Apr. 20, 2007 in related U.S. Appl. No. 10/618,977, filed Jul. 14, 2003.
Baumbach et al., "Local Drug Delivery: Impact of Preassure, Substance Characteristics and Stenting on Drug Transfers into the Arterial Wall," Catherization and Cardiovascular Interventions, Wiley-Liss, Inc., 1999, vol. 47, pp. 102-106.
Series of extracts from the UK Trademarks Register, Apr. 29, 2008.
IUPAC, Compendium of Chemical Terminology (1987).
Table of General Chemical Information, Oct. 12, 2009.
Product information DIOR balloon catheter of Eurocor GmbH, Oct. 1, 2008.
Kalbitz et al., "Modulation der Wirkstoffpenetration in die Haut," Pharmazie, 1996, vol. 51, pp. 619-637.
P. Macke Consigny et al., "Local Delivery of an antiproliferative drug with use of hydrogel-coated angioplasty balloons," J. Vasc. Interv. Radiol., 1994, vol. 5, pp. 553-560.
Drachmann et al., "Neoinitimal thickening after stent delivery of paclitaxel: Charge in composition and arrest of growth over six month," J. Am. Coll. Cardiol., 2000, vol. 36, pp. 2325-2332.
Abstracts From the 70th Scientific Sessions, Circulation, Oct. 21, 1997, 96 Suppl. 1: 1-288.
Van Belle, E. et al., "Passivation of metallic stents after arterial gene transfer of phVEGF165 inhibits thrombus formation and intimal thickening," J. Am. Coll. Cardiol., 1997, vol. 29, pp. 1371-1379.

Versuchsbeschreibungen (D44) ("Description of experiments"), Jul. 9, 2010.
Affidavit (D46), Jul. 9, 2010.
Final Report Study ACL435-43 (D47), May 14, 2009.
Summary Data Biotronik SE & Co. KG (D48), Jul. 9, 2010.
Submission BpatG (Ceramide Balloon Catheter) MLA HLA (D49), Jul. 9, 2010.
German Translation of Gericht zu's Gravenhage, 245392/HA ZA May 2016 (D49A).
Press release of Jan. 17, 2007 regarding patent infringement suit (D49C).
Mortimer, C. et al., Basiswissen Chemie (excerpt) (1987) (D50).
Summons to attend Oral Proceedings dated Jun. 4, 2010 (D51).
Gershlick et al., "Inhibition of Restenosis with a Paclitaxel-Eluting, Polymer-Free Coronary Stent: The European evaluation of pacliTaxel Eluting Stent (ELUTES) Trail," Circulation, 2004, vol. 109, pp. 487-493.
Indolfi et al., "Smooth Muscle Cell Proliferation Is Proportional to the Degree of Balloon Injury in a Rat Model of Angioplasty," Circulation, 1995, vol. 92, pp. 1230-1235.
Manderson et al., "Balloon Catheter Injury to Rabbit Cartoid Artery. I. Changes in smooth muscle phenotype," Artheriosklerosis, 1989, vol. 9, pp. 289.
Data Supplement to R. Charles et al., Circulation Research, 2000, vol. 87, pp. 282.
Stemberger, Axel Dr., "Coating for bio-material to be used e.g. as sutures," Retrieved from Espacenet on Nov. 19, 2010; English Abstract of DE 4435652.
Stemberger, Axel, Dr., "Coating for bio-material insertable into the bloodstream or tissue of the human body," Retrieved from Espacenet on Nov. 19, 2010; English Abstract of DE 19514104.
Stemberger, Axel, Dr., "High efficiency local drug delivery," Retrieved from Espacenet on Nov. 19, 2010; English Abstract of DE 69925936.
Morris, R. E. et al., "Method of treating hyperproliferative vascular disease using rapamycin, eventually in combination with mycophenolic acid," Retrieved from Espacenet on Nov. 19, 2010; English Abstract of EP0551182.
Kaufmann, G. et al., "Process for producing a plastic cladding component and cladding component produced especially by said process," Retrieved from Espacenet on Nov. 19, 2010; English Abstract of WO9625282.
Notice of Opposition to a European Patent. Patent No. 1 539 266 B1 filed by Fish & Richardson on behalf of Boston Scientific Limited. Received in the EPO on Jul. 29, 2008 (49 pages).
Notice of Opposition. Objection to European Patent EU Patent 1 539 266 B1 filed by Karin Lindner-Vogt, European Patent Attorney on behalf of Opponent Biotronik VI Patent AG. English language (40 pages) and German languages (40 pages). Received in the EPO on Dec. 12, 2008. (Total pages 80).
Evidence and Arguments in support of the grounds for opposition. Filed by Jacobacci & Partner on behalf of Opponent Invatec S.p.A. Proprietor: Bayer Schering Pharma Aktiengesellschaft. In re: Opposition against EP-B-1 539 266. Received in the EPO on Jan. 19, 2009. (7 pages).
Notice and Statement of Grounds of Opposition against EP 1 539 266 filed by Williams Powell on behalf of Opponent Cook Incorporated. Date: Jan. 8, 2009. (33 pages).
Opposition against EP 1 539 266 filed by Hoffmann-Eitle on behalf of Peter Klusman Jan. 9, 2009. (7 pages).
Formal objection against EP Patent EP 1 539 266 B1 filed by ABK Patent, Trademark and Designs Attorneys on behalf of Eurocor GmbH. Date: Jan. 6, 2009. In the German language. (45 pages).
Formal objection against EP Patent EP 1 539 266 B1filed by ABK Patent, Trademark and Designs Attorneys on behalf of Eurocor GmbH. Date: Jan. 6, 2009. In the English language. (45 pages).
Reply to the Notices by Bayer Schering Pharma AG. Main Request and as Auxiliary Request I through IV. In the English language. Date: Nov. 23, 2009. (18 pages).
Reply by Bayer Schering Pharma AG. Main Request, Auxiliary Request II, III and IV. In the English language. Date: Nov. 23, 2009. (22 pages).

Reply to the Notices filed by Weickmann & Weickmann on behalf of the Proprietor Bayer Schering Pharma AG. Date: Nov. 23, 2009. In the German language. (37 pages).

Documents submitted in view of the new Auxiliary Requests filed by Fish & Richardson on behalf of Boston Scientific Limited. Date: Mar. 10, 2010. (33 pages).

Summons to oral proceedings in compliance with Rule 115(1) European Patent Convention EPC issued by the EPO with comments to help parties to systematically prepare for the proceedings. Dated Sep. 1, 2010. Application No./Patent No. 03750300.0/1521/1539266. In the languages of English and German. (46 pages).

A pleading for the oral hearing on Feb. 16, 2011 submitted to the EPO filed by ABK Patent, Trademark and Designs Attorneys on behalf of Eurocor GmbH. Dated: Jan. 6, 2011. Re: New Documents Filed. In the language of English. (4 pages).

A pleading for the oral hearing on Feb. 16, 2011 submitted to the EPO by ABK Patent, Trademark and Designs Attorneys on behalf of Eurocor GmbH. Dated: Jan. 6, 2011. Re: New Documents Filed. In the language of German. EP Patent No. 1539266 B1. (4 pages).

Admissibility of the claims of the patent owner submitted to the EPO by ABK Patent, Trademark and Designs Attorneys on behalf of Eurocor GmbH. Dated: Jan. 4, 2011. EP Patent No. 1539266 B1. In language of English. (12 pages).

Admissibility of the claims of the patent owner submitted to the EPO by ABK Patent, Trademark and Designs Attorneys on behalf of Eurocor GmbH. Dated: Jan. 4, 2011. EP Patent No. 1539266 B1. In the language of German. (12 pages).

A pleading for the oral hearing on Feb. 16, 2011 submitted to the EPO according to Rule 115 (1) EPC by ABK Patent, Trademark and Designs Attorney on behalf of Eurocor GmbH. Dated: Jan. 4, 2011. In the language of English. EP Patent No. 1539266 B1. (4 pages).

A pleading for the oral hearing on Feb. 16, 2011 submitted to the EPO according to Rule 115 (1) EPC by ABK Patent, Trademark and Designs Attorney on behalf of Eurocor GmbH. Dated: Jan. 4, 2011. In the language of German. EP Patent No. 1539266 B1. (4 pages).

A submission for the oral hearing on Feb. 16, 2011 provided to the EPO according to Rule 115 (1) EPC by ABK Patent, Trademark and Designs Attorney on behalf of Eurocor GmbH. Dated: Jan. 4, 2011. In the language of English. EP Patent No. 1539266 B1. (20 pages).

A submission for the oral hearing on Feb. 16, 2011 provided to the EPO according to Rule 115 (1) EPC by ABK Patent, Trademark and Designs Attorney on behalf of Eurocor GmbH. Dated: Jan. 4, 2011. In the language of German. EP Patent No. 1539266 B1. (20 pages).

A further pleading for the oral hearing on Feb. 16, 2011 submitted to the EPO by ABK Patent, Trademark and Designs Attorney on behalf of Eurocor GmbH. Dated: Jan. 4, 2011. In the language of English. EP Patent No. 1539266 B1. (4 pages).

A further pleading for the oral hearing on Feb. 16, 2011 submitted to the EPO ABK Patent, Trademark and Designs Attorney on behalf of Eurocor GmbH. Dated: Jan. 4, 2011. In the language of German. EP Patent No. 1539266 B1. (4 pages).

Newly submitted documents. Data Supplement to the scientific publication D4'n submitted to the EPO by ABK Patent, Trademark and Designs Attorney on behalf of Eurocor GmbH. Dated: Jan. 6, 2011. In the language of English. EP Patent No. 1539266 B1. (8 pages).

Newly submitted documents. Data Supplement to the scientific publication D4'n submitted to the EPO by ABK Patent, Trademark and Designs Attorney on behalf of Eurocor GmbH. Dated: Jan. 6, 2011. In the language of German. EP Patent No. 1539266 B1. (8 pages).

Correspondence dated Jan. 7, 2011. Submitted to the EPO by ABK Patent, Trademark and Designs Attorney on behalf of Eurocor GmbH. Re: Updated list of documents cited in the proceedings. In the languages of English and German. EP Patent No. 1539266 B1. (2 pages).

Further submissions for the hearing before the Opposition Division of the EPO. Re: Submitted documents. Submitted to the EPO by ABK Patent, Trademark and Designs Attorney on behalf of Eurocor GmbH. Re: Updated list of documents cited in the proceedings. In the languages of English and German. EP Patent No. 1539266 B1. Dated Jan. 12, 2011. (10 pages).

Submission by Bayer Schering Pharma. Claims modified in compliance with the main request and the auxiliary request I-IX supplied on the ruling dated Oct. 5, 2010. Exhibits, Main Request and auxilary request I-IX. (pp. 78).

Submission by Bayer Schering Pharma. Claims modified in compliance with the main request and the auxiliary request I-IX supplied on the ruling dated Oct. 5, 2010. (38 pages).

A further submission for the hearing before the Opposition Division of the EPO on Feb. 14, 2011. Submitted to the EPO on Jan. 14, 2011 by ABK Patent, Trademark and Designs Attorney on behalf of Eurocor GmbH. Re: Updated list of documents cited in the proceedings. In the language of English. EP Patent No. 1539266 B1. (16 pages).

A further submission for the hearing before the Opposition Division of the EPO on Feb. 14, 2011. Submitted to the EPO on Jan. 14, 2011 by ABK Patent, Trademark and Designs Attorney on behalf of Eurocor GmbH. Re: Updated list of documents cited in the proceedings. In the language of German. EP Patent No. 1539266 B1. (6 pages).

Submission to the EPO by August & Debouzy Avocats on behalf of Invatek S.p.A. Dated Jan. 14, 2011. (2 pages).

Submissions in preparation for oral proceedings of Feb. 16, 2011. Submitted to the EPO by Williams Powell on behalf of Opponent IV Cook Inc. Dated: Jan. 14, 2011. (5 pages).

Submissions in preparation for oral proceedings of Feb. 16, 2011. Submitted to the EPO by Williams Powell on behalf of Opponent IV Cook Inc. Dated: Jan. 31, 2011. (6 pages).

Communication from the Examining Division of the European Patent Office issued on Sep. 15, 2005 in EP Application No. 03 750 300.0/1219. EP Patent No. 1539266.

Annex to the Communication from the Examining Division of the European Patent Office issued on Sep. 15, 2005 in EP Application No. 03 750 300.0/1219. EP Patent No. 1539266.

Reply and claims filed Jan. 13, 2006 in response to the Communication from the European Patent Office dated Sep. 15, 2005 in EP Application No. 03 750 300.0-1219. EP Patent No. 1539266.

English Translation of DE4225553 C1, 2011.

Atkins, Peter, "Chapter 7: Simple Mixtures," Physical Chemistry, $6^{th}$ ed., 1997, pp. 176-186.

Leo, Albert et al., "Partition Coefficients and Their Uses," Chemical Reviews, Dec. 1971, vol. 71, No. 6, pp. 525-616.

Ulicky, L. et al., "Nernst's Distribution Law," Comprehensive Dictionary of Physical Chemistry, pp. 266-267, 1987.

Yushmanov, Victor E. et al., "Dipyridamole Interacts with the Polar Part of Cationic Reversed Micelles in Chloroform: 1H NMR and ESR Evidence," Journal of Colloid and Interface Science, 1997, vol. 191, pp. 384-390.

Gold, Victor et al., "Amount of Substance Concentration," Compendium of Chemical Technology: International Union of Pure and Applied Chemistry Recommendations, 1987, p. 19.

Frank D. Kolodgie et al., Local delivery of ceramide for restenosis: Is there a future for lipid therapy? Circulation Research, Aug. 18, 2000, pp. 264-267.

Johnathan D. Adams et al., "Taxol: a history of pharmaceutical development and current pharmaceutical concerns," Journal of the National Cancer Institute Monographs, 1993, pp. 141-147, No. 15.

Jackson et al., "Current usage of contrast agents, anticoagulant and antiplatelet drugs in angiography and angioplasty in the UK," Clinical Radiology, 1995, pp. 699-704, vol. 50, No. 10.

Elsevier Science Publishers, Amsterdam, NL; Jackson D.M. A. et al Current usage of contrast agents, anticoagulant and antiplatelet drugs in angiography and angiRplasty in the UK. retrieved from STN Database accession No. 95327068 XP002226116, 1995.

International Preliminary Examination Report for PCT/DE2003/002871, 2004.

International Preliminary Examination Report for PCT/DE2001/04782, Jun. 24, 2003.

International Search Report for EP 06 00 1041, Search Date: Apr. 11, 2006.

International Search Report for EP 06 00 1042, Search Date: Apr. 10, 2006.

International Search Report for EP 06 00 1040, Search Date: Apr. 11, 2006.

International Search Report for PCT/DE01/04782, Search Date: Dec. 27, 2002.
International Search Report for PCT/EP03/10480, Search Date: Feb. 20, 2004.
International Search Report for PCT/DE03/02871, Search Date: Feb. 17, 2004.
Brunner, H. et al., "Synthesis and in vitro testing of hematoporphyrin type ligands in platinum (II) complexes as potent cytostatic and phototoxic antitumor agents," Inorganica Chimica Acta, 1997, vol. 264, pp. 67-79.
Bult, H., "Restenosis: a challenge for pharmacology," TIPS, Jul. 2000, vol. 21, pp. 274-279.
Coomber, B. L. et al., "In vitro endothelial wound repair: Interaction of cell migration and proliferation," Arteriosclerosis, Mar. 1990, vol. 10, No. 2, pp. 215-222.
Dichek, D. A. et al., "Seeding of Intravascular stents with genetically engineered endothelial cells," Circulation, 1989, vol. 80, No. 5, pp. 1347-1353.
Elke M: Kontrastmittel in der radiologischen Diagnostik, pp. 113-119, 3$^{rd}$ edition, Georg Thieme Verlag Stuttgart New York, 1992.
English Translation of Elke M: Kontrastmittel in der radiologischen Diagnostik, pp. 113-119, 3$^{rd}$ edition, Georg Thieme Verlag Stuttgart New York, 1992.
Hamm, C. W. et al., "Guideline: Diagnostic Heart Catheter Examination," Clin Res Cardiol, 2008, vol. 97, pp. 475-512.
English Translation of Hamm, C. W. et al., "Guideline: Diagnostic Heart Catheter Examination," Clin Res Cardiol, 2008, vol. 97, pp. 475-512.
Hou, D. et al., "Intrapericardial paclitaxel delivery inhibits neointimal proliferation and promotes arterial enlargement after porcine coronary overstretch," Circulation, 2000, vol. 102, pp. 1575-1581.
Khan, I. A. et al., "The Intra-vascular stent as a site-specific local drug delivery system," Drug Development and Industrial Pharmacy, 2005, vol. 31, pp. 59-78.
Lamba, N. M. K. et al., Polyurethanes in Biomedical Applications Chapter 4, "Structure and Physical Characterization of Polyurethanes," 1998, CRC Press.
Lübbe, A. S. et al., "Preclinical experiences with magnetic drug targeting: Tolerance and Efficacy," Cancer Research, 1996, vol. 56, pp. 4694-4701.
Nicolaou, K. C. et al., "Design, synthesis and biological activity of protaxols," Nature, Jul. 29, 1993, vol. 364, pp. 464-466.
Schmitz, S. A. et al., "Superparamagnetic iron oxide-enhanced MRI of atherosclerotic plaques in Watanabe Hereditable Hyperlipidemic Rabbits," Investigative Radiology, Aug. 2000, vol. 35, No. 8, pp. 460-471.
English Abstract of JP-06 063145, "Balloon Catheter for intravascular dosing," Buaayu KK, Patent Abstracts of Japan, Publication Date: Mar. 8, 1994.
English Abstract of JP-6 063145, "Balloon Catheter for Intravascular dosing," Buaayu KK, Thomson Innovation, Publication Date: Mar. 8, 1994.
English Abstract of JP-07 328124, "Medicine dosing catheter," Terumo Corp., Patent Abstracts of Japan, Publication Date: Dec. 19, 1995.
Patent Family Listing for JP-2001 508320 (Publication Date: Jun. 26, 2001), Thomson Innovation.
Patent Family Listing for JP-2002 536058 (Publication Date: Oct. 29, 2002), Thomson Innovation.
English translation of Decision of Final Rejection, Japanese Application No. 2004 235694, issued Mar. 9, 2010.
English Translation of JP 36371777 (Publication Date: Mar. 23, 2005), Thomson Innovation.
Submission by Eurocor, filed Feb. 18, 2011, in EPO Opposition against EP 1 539 266.
English Translation of Submission by Eurocor, Feb. 18, 2011, in EPO Opposition against EP 1 539 266.
Minutes of Oral Hearing, May 3, 2011, in Opposition against EP 1 539 266.
English translation of Minutes of Oral Hearing, May 3, 2011, in Opposition against EP 1 539 266, issued May 3, 2011.
EPO Decision to revoke EP 1 539 266, in EPO Opposition against EP 1 539 266.
English Translation of Decision to revoke the EP Patent, in EPO Opposition against EP 1 539 266.
Grounds of Appeal, filed Sep. 12, 2011, by Bayer Pharma AG, in EPO Opposition against EP 1 539 266 (with Main and Auxiliary Requests).
English Translation of Grounds of Appeal, filed Sep. 12, 2011, by Bayer Pharma AG, in EPO Opposition against EP 1 539 266 (with Main and Auxiliary Requests).
Response to Appeal, filed Oct. 13, 2011 by Boston Scientific, in EPO Opposition against EP 1 539 266.
Response to Appeal, filed Jan. 20, 2012 by Cook Inc., in EPO Opposition against EP 1 539 266.
Response to Appeal, filed Jan. 26, 2012 by Dr. Peter Klusmann, in EPO Opposition against EP 1 539 266.
Cancellation Action against DE 203 21 606 filed in the German Patent Office by Eurocor (Sep. 6, 2010).
English Translation of Cancellation Action against DE 203 21 606 filed in the German Patent Office by Eurocor (Sep. 6, 2010).
Submission by Bayer Schering Pharma (BSP) filed Feb. 25, 2011 in Cancellation Action against DE 203 21 606.
Thomson Innovation, Patent Record View, Publication Date: Sep. 22, 1998; English abstract of JP-10 509691.
Thomson Innovation, Patent Record View, Publication Date: Jan. 19, 1995; English abstract of JP-7 500585.
English Translation of Submission by Bayer Schering Pharma (BSP) filed Feb. 25, 2011 in Cancellation Action against DE 203 21 606.
Submission by Eurocor filed Apr. 20, 2011 in Cancellation Action against DE 203 21 606.
English Translation of Submission by Eurocor filed Apr. 20, 2011 in Cancellation Action against DE 203 21 606.
Submission by Bayer Schering Pharma (BSP) filed Sep. 30, 2011 in Cancellation Action against DE 203 21 606.
English Translation of Submission by Bayer Schering Pharma (BSP) filed Sep. 30, 2011 in Cancellation Action against DE 203 21 606.
Submission by Eurocor filed Dec. 2, 2011 in Cancellation Action against DE 203 21 606.
English Translation of Submission by Eurocor filed Dec. 2, 2011 in Cancellation Action against DE 203 21 606.
Office Action issued Aug. 16, 2011 in U.S. Appl. No. 12/835,420.
Office Action issued Oct. 13, 2011 in U.S. Appl. No. 11/763,116.
Office Action issued Dec. 16, 2011 in U.S. Appl. No. 12/835,414.
Office Action issued Feb. 16, 2012 in U.S. Appl. No. 12/782,989.
Office Action issued Mar. 9, 2012 in U.S. Appl. No. 12/835,420.
Judgment of Sep. 16, 2011 (Paper No. 52) from Interference No. 105,787.
Redeclaration of Interference (Paper No. 48) issued Sep. 13, 2011.
Applicants' Amendment of Sep. 12, 2011 (Paper No. 47), filed in U.S. Appl. No. 11/763,125, and cited in the Judgment of Sep. 16, 2011 in Interference No. 105,787.

* cited by examiner

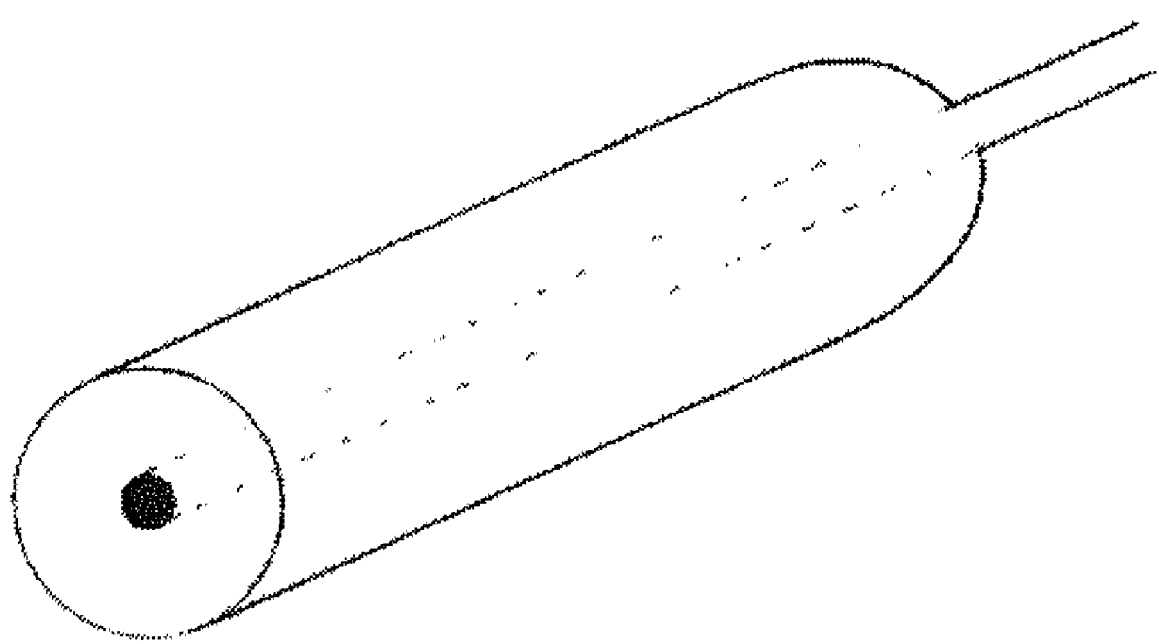

MEDICAL DEVICE FOR DISPENSING MEDICAMENTS

This invention relates to a medical apparatus that releases drugs for the selective therapy of specific tissues or organ parts and to a method of manufacturing such drug-coated devices.

Numerous diseases do not affect the entire organism at the same time but are restricted to specific tissues, often even to very limited individual tissue areas or organ parts. Examples can be found among tumor, joint and vascular diseases.

Pharmacotherapy of such diseases generally is effected by oral or intravenous administration of drugs that spread throughout the body and cause undesirable side effects in healthy tissues and organs, especially when the disease to be treated is in a severe stage, which limit the therapeutic application. The diseased tissues could be treated either selectively using drugs that specifically bind to diseased tissue (e.g. antibodies) while the administration path is maintained, or by selective administration, e.g. direct injection into the diseased tissue or supply via a catheter to the blood vessels that feed the diseased tissue. In case of selective administration may problems arise due to the short period of time during which the drugs are efficacious and the invasive administration paths, as repeated administration is not an option. When drugs are selectively administered via the bloodstream that feeds the diseased tissue, there is the additional problem that the drugs are insufficiently extracted when the blood or active agent solution swiftly flows through the blood vessels.

These problems used to be addressed by various pharmaceutical preparations with sustained release of the active agent, drug-releasing implants or selective access paths that stay operational for a longer period of time such as implanted catheters, etc.

It is known that the surface of medical equipment inserted into the body, in particular, of catheters, can be coated with agents that enhance gliding quality or prevent blood coagulation but have no therapeutic effect.

In addition, catheters are equipped with special devices for injecting drugs into the arterial wall, for example, using needles or a perforation of the catheter wall that sits adjacent to the vessel wall and through which the drug is injected at high pressure.

Other principles are based on extending the contact time between the arterial wall and an active agent preparation administered via the catheter by either blocking the blood flow for a sufficient period of time, e. g. using dual balloon catheters in which the active agent solution is contained in a chamber between the balloons, or by voids between a toric outer wall of the balloon allowing a limited flow of blood through a canal that passes through the balloon.

According to U.S. Pat. No. 5,102,402, drugs in the form of microcapsules are inserted into preformed recesses of balloon catheters for delayed release of the active agent. When the balloon is inflated, the microcapsules are to be pressed against the vessel wall, remain there and slowly release the active agent(s). Many authors propose to apply drugs embedded in hydrogel onto balloon catheters while they do not specify the function of the hydrogel, i. e. to act as an adhesive, to improve the gliding quality, or for controlled drug release.

A disadvantage of the products mentioned above is their complex structure, which causes production, quality control, and cost problems and forces additional aggravating working steps on doctors and patients when applied. Some of the methods mentioned may result in undesirable vascular damage in excess of the intended dilatation of the vessel. Another setback is that each measure aimed at extending contact time entails another reduction in blood and oxygen supply to the downstream tissues.

For the sake of completeness, we also refer to a device for preventing restenosis as described in WO 01/24866 that is coated with a lipid ceramide substance derived from natural cell membranes. This substance is used because of its affinity to cell walls that is not found in common drugs. Experts in the field continue to state that restenosis prevention using drugs requires release of the active agent over a period of several days.

The problem underlying the present invention is to provide a device for the release of drugs into specific tissue areas or organ parts that has a strong therapeutic effect without damaging healthy tissue, which is sufficiently well tolerated, and can be produced and applied with a minimal effort.

This problem is solved according to the invention by a medical device that releases drugs for the selective therapy of specific diseased tissues or organ parts, characterized in that lipophilic, largely water-insoluble drugs that bind to any tissue components adhere to the surfaces of devices that come into contact with the diseased tissue by being pressed against it at least for a short time and immediately release the active agent when in contact with tissue, and of a method for producing such a device characterized in that the lipophilic drugs and excipients in a solution, suspension or emulsion medium are applied using an immersion, spreading, or spraying process or an instrument which delivers a defined volume to the surface of the device while excess media and substances that adhere loosely to the surface are removed.

The invention provides improved drug-carrying balloon catheters or similar medical devices manufactured in a simple process that are highly versatile and facilitate the immediate release of active agents. Surprisingly, and contrary to the currently acknowledged opinion, no continuing release of the active agent from an inert matrix (polymer, hydrogel, microcapsule, etc.) and no special chemical or physical state of the active ingredients is required or useful. Therefore, no sophisticated techniques for producing or controlling depot formulations are required.

Coating balloons on catheters with drugs according to this invention is particularly useful because there is a frequent need for treatment after blood vessels or other passages in the body were dilated with balloons to prevent stenosis or an occlusion of the lumen created by the pressure of the balloon, to limit tumor growth or to enhance healing processes including the formation of collateral circulation. This can be achieved by drugs that become effective in the immediate vicinity of the balloon surface. The drugs firmly adhere to the balloon while passing through arteries with an intense blood flow on their way to their target until the balloon is inflated, and an effective dose is released in the short time (sometimes just a few seconds) during which the inflated balloon is in contact with the tissue, absorbed by the tissue in such a way that the blood flow that resumes immediately after the balloon is deflated does not rinse it off.

The subjects for coating are wires of the invention used to guide catheters, needles and catheters or catheter parts that are pressed against the diseased tissue at least for a short time. Preferred catheter materials are polyamides, polyamide mixtures and copolymers, polyethylene terephthalate, polyethylene and copolymers, polyurethane, natural rubber and its derivatives. The lengths and diameters of the catheter or balloon areas designated for pharmacological treatment are not of any decisive importance for their application as the dosage is calculated in µg of active agent/mm$^2$ of surface area. For example, balloons with diameters ranging from 2 to 4 mm and lengths ranging from 1.0 to 4.0 cm are commonly used for coronary dilatation. Balloons up to >20 mm in diameter and up to >10 cm in length can be used for other vessels. The surfaces to be coated may be smooth (i.e. without a special structure for absorbing the active agents), roughed up or comprise any structure; while no special surface structures are required for the active agents to adhere, such structures also do not impede adhesion. Adhesion of the active agents to the balloon surfaces is exclusively caused by selecting suitable solvents and, optionally, adding substances that influence adhesion. It is even surprisingly strong on completely smooth balloon surfaces.

All surfaces can additionally be coated with substances that improve the gliding quality of the products, prevent blood from coagulating on the surface or improve any other properties of these medical products have but the materials used for coating do not have to be released into the environment and this additional coating does not noticeably reduce the release of the active agents for treatment of the target tissue and thus the product's efficacy.

Balloon catheters are formed by dilating a segment of 1 cm to ca. 10 cm length of very thin plastic tubes. The dilated, very thin-walled balloon membrane is then folded several times along the catheter axis and wrapped tightly around the catheter axis so that the dilated area, when folded, is only slightly greater in diameter than the rest of the catheter. The tight folding of the balloon membrane is required for passing the balloon catheter through access ports, guiding catheters and heavily stenosed sections of blood vessels.

The balloons of catheters can be coated when folded or when unfolded. The process always provides an intact and sufficiently uniform surface coating, and the active agents adhere to the surface of the balloon catheter even when it is refolded after being coated when unfolded.

A balloon that was coated when unfolded is produced without any impact on the coating, for example by using balloon membranes with preformed folds and bends whose structure is not lost due to dilatation and which allow the balloon membrane to refold at least loosely when the pressure is discharged from the balloon without requiring an external force as primary cause. It is only after this prefolding that the preformed folds are compressed by external pressure or by a vacuum. Folds are in no way required to hold the active agent. In addition refolding can be achieved using minor mechanical force by very smooth materials, and the tools used may also be wetted by slippery biocompatible liquids in which the active ingredients do not or, at least, do not well dissolve.

In accordance with another variant of the invention, the balloons of readily folded balloon catheters are coated by dipping them into low-viscosity active agent solutions. Solvent and active agent penetrate into the extremely dense folds where they form a surprisingly uniform coat that contains a reproducible dose and is not damaged by any subsequent step. The solution or, after the solvent has dried, the coat that adheres to the outer surface may be left there or may be removed in another step so that only the active agent portion that sits inside the folds of the balloon is retained.

After coating, when the balloon is folded, a stent can be pulled over the balloon catheter and firmly pressed onto it. The only step still required is sterilization, e.g. using ethylene oxide.

The work cycle laid out like this is extremely simple, hardly susceptible to failures, and can be carried out even with mechanically, chemically and physically sensitive coating materials. It was found that coating using this method does not result in any undesirable loosening or sticking together of the folds and that the active agent applied in this way adheres firmly enough to not be rinsed off by the bloodstream but releases most of the active agent when the balloon is inflated in the target tissue.

Suitable drugs are lipophilic, mostly water-insoluble and strongly acting drugs that bind to any tissue components. Drugs are called lipophilic when their butanol to aqueous buffer solution (pH 7) distribution ratio is 0.5, preferably 1 and particularly preferred 5, or when their octanol to aqueous buffer solution (pH 7) distribution ratio is 1, preferably 10, and particularly preferred greater than 50. Alternatively, or in addition to this, the drugs should reversibly and/or irreversibly bond to cell components at percentages greater than 10%, preferably greater than 50%, and particularly preferred greater than 80%. Preferred are substances that inhibit cell proliferation or inflammatory processes, or antioxidants such as Paclitaxel and other taxanes, Rapamycin and related substances, tacrolimus and related substances, corticoids, sexual hormones (estrogen, estradiol, antiandrogens) and related substances, statins, epothilones, probucol, prostacyclins, angiogenesis inducers, etc.

These substances are preferably present as a dry solid or as an oil on the surfaces of the various medical products. Preferred are the smallest particle sizes (mostly <5 microns, preferably <1 microns, particularly preferred <0.1 microns), particularly preferred are amorphous non-crystalline structures of the finest particle size that dissolve fast upon contact with tissue due to their large surface area and despite the generally poor water-solubility of the drugs and do not function as microcapsules, i. e. dissolve spontaneously and fast. It is sufficient that an effective dose is present in the form of smallest or amorphous particles; larger particles hardly contribute to the active agent concentration in the tissue but do not cause any interference. The dosage depends on the desired effect and the efficacy of the drug used. It may be up to 5 $\mu g/mm^2$ and this value does not even constitute an upper limit. It is easier to handle smaller dosages.

Good adhesion to the surfaces of catheters, needles or wires on an improved absorption by the tissues is achieved by embedding strongly lipophilic active agents with poor water solubility in a readily water-soluble matrix substance. Suitable matrix substances are low-molecular (molecular weight <5000 D, preferably <2000 D) hydrophilic substances such as contrast agents and dyes used in vivo for various diagnostic procedures in medicine, sugar and related substances such as sugar alcohols, low-molecular polyethylene glycols, biocompatible organic and inorganic salts such as, for example, benzoates, salts and other derivatives of salicylic acid, etc. Examples of contrast agents are iodinated X-ray contrast agents and paramagnetic chelates, examples of dyes are indocyanine green, fluorescein, and methylene blue. Excipients may also improve shelf life of the products, cause specific additional pharmacological effects or be instrumental for quality control.

In another embodiment of the invention, the pharmaceutical active agents can be adsorbed to particles or applied to the surfaces of suitable medical products with a low-molecular matrix. Suitable particles once again are diagnostics known to be biocompatible such as ferrites and various contrast agents for sonography.

Excipients of any kind can be used at lower or higher doses than the active ingredients.

The medical products are coated using solutions, suspensions, or emulsions of the drugs and excipients mentioned above. Suitable media for solution, suspension or emulsion are, for example, ethanol, isopropanol, ethyl acetate, diethyl ether, acetone, dimethyl sulfoxide, dimethyl formamide, glycerin, water or mixtures thereof. Solvent selection is based on the solubility of the active agents and adjuvants, the wetting of the surfaces to be coated and the effect on the structure of the coating and particles remaining after evaporation of the solvent, their adhesion to the surface and active agent transfer to the tissue in very short contact times.

Coating can be carried out by immersing, spreading, applying with devices which deliver a defined volume to the surface or spraying at various temperatures and, optionally, vapor saturation of the solvents in the atmosphere. The procedure can be repeated several times using different solvents and excipients as may be required.

The balloons of folded balloon catheters ready for use can be given a surprisingly uniform, reproducible, dose-controllable coating without impairing catheter functionality by immersing them in solutions containing the active agent(s) or by other measures. When the balloons are repeatedly immersed in unsaturated active agent solutions, the active agent applied previously is not completely stripped off; instead, the active agent content of the balloons is increased in a reproducible manner.

Excess solution or excess substances from the coating solution that are loosely attached to the exterior can be removed with simple methods without impairing the efficacy of the coating.

The various types of medical devices designed and manufactured according to the invention come into short-term contact with the tissue, i. e. for a few seconds, minutes, or hours. It is desirable in some cases to pharmacologically treat the tissue with drugs in the immediate vicinity of the medical product, e. g. to prevent excess growth as a response to an injury or to reduce tumor growth, to enhance neovascularization or diminish inflammatory reactions. In all these cases, high local drug concentrations can be achieved for an astonishingly long time using the method described above. A major advantage is the extraordinary versatility of uses of the products and methods described.

A preferred application is to reduce hyperproliferation of vessel walls induced by dilatation with balloon catheters. This can be achieved when stents are implanted by coating these stents with drugs, but only for the vessel section covered by the stent. The coated balloon catheters also treat any areas at short distance in front of and just behind the stent that need treatment, they can treat the section where a stent has been implanted without requiring another stent implantation and vessels in which no stent is to be or can be implanted. An advantage as compared to the stents that release a drug over a long period of time is improved healing and simultaneous good inhibition of hyperproliferation and a reduced risk of thrombosis.

Several embodiments of the invention will be described below with reference to examples regarding the coating of balloon catheters, adhesion of the coating in the bloodstream, restenosis inhibition and active agent content of the catheters.

BRIEF DESCRIPTION OF THE DRAWING

FIG. 1 shows a catheter with an expanded balloon on which a coating of this invention can be applied.

EXAMPLE 1

Coating an Expanded Balloon Catheter with Paclitaxel in Ethyl Acetate

Balloon catheters made by BMT, Oberpfaffenhofen/Munich, Germany, product name Joker Lite, balloon dimensions 2.5 mm by 20 mm, are inflated to the maximum and immersed full length for 1 minute in ethyl acetate, 18.8 mg Paclitaxel per ml, +1% pharmaceutical olive oil, dried: Paclitaxel content 39 micrograms (after extraction with ethanol, HPLC).

EXAMPLE 2

Coating a Folded Balloon Catheter with Paclitaxel in Ethyl Acetate

Balloon catheters made by BMT, Oberpfaffenhofen/Munich, Germany, product name Joker Lite, balloon dimensions 2.5 mm by 20 mm, are immersed full length in folded condition for 1 minute in ethyl acetate, 18.8 mg Paclitaxel per ml, +1% pharmaceutical olive oil, and dried:

Paclitaxel content 69 micrograms.

EXAMPLE 3

Coating a Folded Balloon Catheter with Paclitaxel in Ethyl Acetate
a) Balloon catheters made by BMT, Oberpfaffenhofen/Munich, Germany, product name Joker Lite, balloon dimensions 2.5 mm by 20 mm, are immersed full length in folded condition for 1 minute in ethyl acetate, 16.6 mg Paclitaxel per ml, and dried for 4 hours: Paclitaxel content 54 micrograms.
b) Same procedure, but additional two times immersed for 5 seconds with 1 hour drying time after each immersion process in solution A (=3.33 ml ethyl acetate +100.0 mg of Paclitaxel): Paclitaxel content 126 micrograms.
c) Same procedure, but additional four times immersed for 5 seconds with 1 hour drying time after each immersion process in the same solution: Paclitaxel content 158 micrograms.

EXAMPLE 4

Coating a Balloon Catheter with Paclitaxel in Acetone

Dissolve 350 mg of Paclitaxel in 9.0 ml of acetone; balloon catheters made by BMT, Oberpfaffenhofen/Munich, Germany, product name Joker Lite, balloon dimensions 2.5 mm by 20 mm, are inflated to the maximum and immersed full length for 1 minute and removed. The solvent is dried for 12 hours at room temperature. Then the balloon is deflated and folded in the common way using a PTFE-coated tool. Optionally, one can crimp a stent of suitable dimensions onto the balloon: 29 micrograms of Paclitaxel on the balloon.

EXAMPLE 5

Coating a Balloon Catheter with Paclitaxel in Acetone
a) Immersion of folded balloon catheters made by BMT, product name Allegro, balloon dimensions 2.5 by 20 mm in a mixture of 0.15 ml ethanol +4.5 µl of Ultravist 300 (an X-ray contrast agent made by Schering AG, Berlin, Germany) +1.35 ml of acetone +0.8 mg of Sudan red +30.0 mg of Paclitaxel: The folded balloon sections of the catheters are immersed 5 times, the first time for one minute, then dried for 3 hours, then 4 times at 1 hour intervals for 5 seconds each; subsequently, a stent was crimped on and the catheter was sterilized in the common way using ethylene oxide: Paclitaxel content 172 micrograms, no decomposition products of the active agent were determined using HPLC
b) A saturated aqueous mannitol solution is used instead of Ultravist 300
c) A saturated aqueous sodium salicylate solution (pH 7.5) is used instead of Ultravist 300 d) 5 mg of acetylsalicylic acid are added to the completed solution according to (5a).
e) 5 mg of glycerin are added to the completed solution according to (5a).

EXAMPLE 6

Adhesion of the Active Agent in the Bloodstream 12 balloon catheters made by BMT, product name Allegro, balloon dimensions 2.5 by 20 mm, were used. The folded balloon sections of 6 catheters each were either 5 times immersed in [0.15 ml of ethanol +4.5 ul of Ultravist 300+1.35 ml of acetone +0.8 mg of Sudan red +30.0 mg Paclitaxel] or 5 times in [1.5 ml of ethyl acetate +0.8 mg Sudan red +31.0 mg Paclitaxel], the first time for 1 minute each with 3 hours of drying time, then 4 times for 5 seconds each at 1 hour intervals; then 3 of the folded balloons of each group were gently moved for 5 minutes at 37° C. in 50 ml of human blood and removed to determine the Paclitaxel content: Reduction of mean values (n=3 per coating method) by 5 minutes of movement in blood as compared to 3 control catheters that were not incubated in blood.

| | |
|---|---|
| Acetone: | 12% |
| Ethyl acetate: | 10% |

EXAMPLE 7

Examination of Restenosis Inhibition after Angioplasty and Stent Implantation in Coronary Arteries of Pigs.

Folded balloon catheters of the Joker Lite type made by BMT, 3.5 by 20 mm or 3.0 by 20 mm were immersed for 1 minute either in solution A) 3.33 ml of ethyl acetate (EA)+100.0 mg of Paclitaxel, or in
solution B) 0.45 ml of ethanol +100 ul of Ultravist-370+4.5 ml acetone (ac) +150.0 mg Paclitaxel and dried over night at room temperature. One more (low dose=L) or 4 more (high dose=H) immersion process(es), respectively, were carried out for just five seconds at 1 hour intervals on the next day. Active agent content after 2 immersions in solution (B) averaged 250 µg, after 5 immersions in solution (B) 500 µg, in solution (A) 400 µg.

The catheters coated with Paclitaxel or uncoated were used to implant stents into the left anterior or lateral coronary artery of a total of 22 pigs, and the vessels were slightly overdilated to stimulate restenosis by tissue hyperplasia. The animals were reangiographed after 5 weeks, and the vessel stenosis shown in the angiograms was measured using an automatic computer program.

| Group | Stenosis (%) |
|---|---|
| Uncoated | 50.49 |
| AcL | 20.22 |
| EAH | 36.01 |
| AcH | 0.86 |
| P | .004 |

Quantitative coronary angiography 5 weeks after stent implantation with uncoated and coated catheters; stenosis=reduction of lumen diameter in percent in the area of the stent as compared to the lumen diameter immediately after stent implantation; mean value and statistical significance of the effect of treatment.

EXAMPLE 8

Active Agent Content of the Catheters after Vessel Dilatation and Stent Implantation After stent implantation and removal from the animals, the balloons from Example 7 ca. 3 cm in length were cut off the balloon catheters and placed in 1.5 ml of ethanol. Paclitaxel content was determined using HPLC. All available coated balloons and a selection of uncoated balloons were examined.

Coronary,

| | | |
|---|---|---|
| 3.0 by 20 mm, coating: | Ac high | 38 ± 4 µg (n = 4) |
| | Ac low | 22 ± 5 µg (n = 2) |
| | EEE high | 41 (n = 1) |
| 3.5 by 20 mm, coating: | Ac high | 37 ± 10 µg (n = 8) |
| | Ac low | 26 ± 6 µg (n = 8) |
| | EEE high | 53 ± 9 µg (n = 9) |
| Uncoated (independent of size and vessel area) | | 0.9 ± 1.0 µg (n = 7) |

It follows from Example 6 that a maximum of 10% of the dose is lost before the balloon is inflated and about 10% of the dose remain on the balloon.

EXAMPLE 9

Probucol is added to acetone at a concentration of 100 mg per ml; the solution is used to coat balloon catheters as described in the above examples.

EXAMPLE 10

Rapamycin is dissolved at a concentration of 10 mg/ml in diethyl ether. The balloon sections of the catheters are coated as described in the above examples; after removal from the coating solution, the balloons should be brought into a horizontal position and continuously be turned around their longitudinal axis as soon as possible.

EXAMPLE 11

Epothilone B is dissolved in ethyl acetate at a concentration of 2 mg/ml; the solution is used to coat balloon catheters as described in the above examples.

The invention claimed is:

1. A balloon catheter medical device that releases a drug by immediate release for the selective therapy of specific diseased tissue or an organ part to which said drug will bind, comprising such a drug which is lipophilic, water-insoluble and immediately releasable, adhered to a smooth surface of the balloon of said catheter that comes into contact with the diseased tissue or organ part, which adhered drug when pressed against said tissue or organ part at least for a short time, is immediately released into said tissue or organ part, wherein the concentration of said drug on said surface is up to 5 µg/mm².

2. The device according to claim 1, wherein said balloon catheter comprises a stent.

3. The device according to claim 2, wherein a balloon with preformed longitudinal folds is coated with the drug, and the inclination of said folds to refold is not lost after inflation.

4. The device according to claim 2, wherein a balloon is coated with said drug and comprises smooth material to which said drug adheres sufficiently well to resist forces required for folding, essentially without damage.

5. The device according to claim 2, wherein only the area covered by folds is coated with the drug that was dried after application.

6. The device according to claim 1, wherein said balloon catheter does not comprise a stent.

7. The device according to claim 1, wherein the lipophilic drug is an inhibitor of cell proliferation or inflammatory processes, or an antioxidant.

8. The device according to claim 7, wherein the drug used is paclitaxel or other taxane, rapamycin, tacrolimus, a corticoid, a sex hormone, a statin, an epothilone, probucol, a prostacyclin, or an angiogenesis inducer.

9. The device according to claim 7, wherein the lipophilic drug is present as a dry solid or oil on the surface of the device.

10. The device according to claim 9, wherein the dosage form of the drug includes amorphous structures with particle sizes ranging from <0.1 micron to 5 microns that dissolve quickly due to their large surface area and despite the water-insolubility of the drug.

11. The device according to claim 1, wherein the lipophilic drug is embedded in a readily water-soluble matrix substance to achieve good adhesion to the surface of the device and improve absorption by the tissue.

12. The device according to claim 11, wherein said matrix substance is a low-molecular weight hydrophilic substance with a molecular weight <5000 D.

13. A medical device of claim 12 wherein said drug is paclitaxel and said device is an angioplasty balloon catheter having a smooth balloon surface.

14. The device according to claim 1, wherein the lipophilic drug is absorbed to particles of or applied to the surface of the device with, a low-molecular weight matrix.

15. The device according to claim 1, having a surface additionally coated with a substance that influences the gliding quality of the device or that prevents blood coagulation.

16. A medical device of claim 1 wherein said drug is paclitaxel and said device is an angioplasty balloon catheter having a smooth balloon surface.

17. A method for producing the device according to claim 1, comprising applying the lipophilic drug in a solution, suspension or emulsion medium using an immersion, spreading, or spraying process or an instrument which delivers a defined volume to the surface of the device to provide a coating and removing excess media and substances that adhere loosely to the surface.

18. The method according to claim 17, wherein the coating process is carried out repeatedly to achieve a reproducible increase of the drug content using the same or a different solution, suspension, or emulsion medium and/or excipient.

19. The method according to claim 18, wherein ethanol, isopropanol, ethyl acetate, diethyl ether, acetone, dimethyl sulfoxide, dimethyl formamide, glycerin, water or a mixture thereof is used as solution, suspension, or emulsion medium.

20. The method according to claim 17, wherein a balloon folded ready for use is used as the drug carrier coated prior to or after sterilization with or without a crimped-on stent.

21. The method according to claim 20, wherein the balloon is coated with the lipophilic drug in unfolded condition and then is folded with a lubricating tool optionally wetted with a biocompatible, gliding agent.

22. The method according to claim 17, wherein a stent is attached prior to or after coating of the balloon.

23. The method according to claim 17, wherein the completely coated device is sterilized using ethylene oxide.

24. A method of treating a vascular disease or circulation disturbance comprising administering a device of claim 1 to affected tissue.

25. A method of opening a passage in the body comprising administering a device of claim 1.

26. A balloon catheter having folds in its balloon, comprising a lipophilic, water-insoluble drug which binds to tissue, said drug being adhered to a smooth balloon surface in a fashion wherein it is immediately released upon coming into contact with said tissue, wherein the balloon area covered with folds is coated with said drug which has been dried after application, and wherein the concentration of said drug on said surface is up to 5 µg/mm$^2$.

27. The balloon catheter according to claim 26, further comprising a stent, a needle or a guiding wire.

28. The balloon catheter according to claim 26, comprising in its finally folded state a balloon coated with a low-viscosity active agent solution of said drug, by immersing, spraying or applying via a volume measuring device.

29. The balloon catheter according to claim 26, wherein the lipophilic drug is an inhibitor of cell proliferation or an inflammatory process, or an antioxidant.

30. The balloon catheter according to claim 29, wherein the drug is paclitaxel or other taxane, rapamycin, tacrolimus, a corticoid, a sex hormone, a statin, an epothilone, probucol, a prostacyclin or an angiogenesis inducer.

31. The balloon catheter according to claim 29, wherein the lipophilic drug is present as a dry solid or oil on the surface of the balloon.

32. The balloon catheter according to claim 31, wherein the dosage form of the drug comprises amorphous structures with particle sizes ranging from <0.1 micron to 5 microns that dissolve fast due to their large surface area and despite the water-insolubility of the drug.

33. The balloon catheter according to claim 26, wherein said lipophilic drug is embedded in a readily water-soluble matrix substance to achieve good adhesion to the surface of the balloon and improved absorption by the tissue.

34. The balloon catheter according to claim 33, wherein said matrix substance is a low-molecular weight hydrophilic substance with a molecular weight <5000 D.

35. A balloon catheter of claim 34 wherein said drug is paclitaxel and said device is an angioplasty balloon catheter having a smooth balloon surface.

36. The balloon catheter according to claim 33, wherein said matrix substance is a contrast agent.

37. The balloon catheter according to claim 36, wherein said substance is an iodinated X-ray contrast agent.

38. The balloon catheter according to claim 37, wherein the drug is paclitaxel and the X-ray contrast agent is iopromide.

39. The balloon catheter according to claim 26, wherein said lipophilic drug is absorbed to a particle or applied to the surface of the device with a low-molecular weight matrix.

40. The balloon catheter according to claim 26, having a surface additionally coated with a substance that influences the glidability of the device or that prevents blood coagulation.

41. A balloon catheter of claim 26 wherein said drug is paclitaxel and said device is an angioplasty balloon catheter having a smooth balloon surface.

42. A method for producing the coated balloon catheter according to claim 26, comprising applying the lipophilic drug in a solution, suspension or emulsion medium using an immersion, spreading, or spraying process or a volume measuring device to the surface of a folded balloon, and removing excess media and substances that adhere loosely to the surface.

43. The method according to claim 42, wherein the coating process is carried out repeatedly to achieve a reproducible increase of the drug content using the same or a different solution, suspension, or emulsion medium and/or excipient.

44. The method according to claim 43, wherein ethanol, isopropanol, ethyl acetate, diethyl ether, acetone, dimethylsulfoxide, dimethylformamide, glycerol, water or a mixture thereof is used as solution, suspension, or emulsion medium.

45. The method according to claim 42, wherein a folded and substantially ready for use balloon is used as the drug carrier coated before or after sterilization with or without a crimped-on stent.

46. The method according to claim 42, wherein a stent is connected to the balloon catheter before or after coating.

47. The method according to claim 42, wherein the finally coated balloon catheter is sterilized using ethylene oxide.

48. A method for the treatment of a vascular disease or a dysfunction of circulation comprising administering a catheter of claim 26.

49. A method for opening a passage in the body comprising administering a catheter of claim 26.

50. A method for tumor treatment comprising administering a catheter of claim 26.

51. A balloon catheter medical device that releases a drug by immediate release for the selective therapy of specific diseased tissue or an organ part to which said drug will bind, comprising such a drug which is lipophilic, water-insoluble and immediately releasable, adhered to a surface of the balloon of said catheter that comes into contact with the diseased tissue or organ part, which adhered drug when pressed against said tissue or organ part at least for a short time, is immediately released into said tissue or organ part, wherein the drug is adhered to said surface in a manner resulting in an amount of drug retained on said device of about 10% or less after a time period in which said balloon surface is in contact with said tissue of up to a few minutes, and wherein the concentration of said drug on said surface is up to 5 $\mu g/mm^2$.

52. A balloon catheter of claim 51 wherein said drug is paclitaxel and said device is an angioplasty balloon catheter having a smooth balloon surface.

53. The device of claim 1 wherein the lipophilic drug is present as a dry solid on the surface of the device.

54. The device of claim 53 wherein the lipophilic drug is paclitaxel.

55. The device of claim 53 wherein the dried solid also comprises a contrast agent.

56. The device of claim 55 wherein the dried solid comprises paclitaxel and iopromide.

57. The catheter of claim 26 wherein the lipophilic drug is present as a dry solid on the surface of the device.

58. The catheter of claim 57 wherein the lipophilic drug is paclitaxel.

59. The catheter of claim 57 wherein the dried solid also comprises a contrast agent.

60. The catheter of claim 59 wherein the dried solid comprises paclitaxel and iopromide.

* * * * *

UNITED STATES PATENT AND TRADEMARK OFFICE
CERTIFICATE OF CORRECTION

PATENT NO. : 8,257,305 B2
APPLICATION NO. : 10/528577
DATED : September 4, 2012
INVENTOR(S) : Speck et al.

It is certified that error appears in the above-identified patent and that said Letters Patent is hereby corrected as shown below:

Title Page, Item (56), on Page 4, right column, line 28, under "OTHER PUBLICATIONS", delete "Neointima" and insert -- Neointimal --, therefor.

Title Page, Item (56), on Page 4, right column, line 31, under "OTHER PUBLICATIONS", delete "Neointinal" and insert -- Neointimal --, therefor.

Title Page, Item (56), on Page 5, left column, line 19, under "OTHER PUBLICATIONS", delete "Jounral" and insert -- Journal --, therefor.

Title Page, Item (56), on Page 5, left column, line 34, under "OTHER PUBLICATIONS", delete "Neointimaporliferation" and insert -- Neointimaproliferation --, therefor.

Title Page, Item (56), on Page 5, left column, line 47, under "OTHER PUBLICATIONS", delete "pharmazeutishchen" and insert -- pharmazeutischen --, therefor.

Title Page, Item (56), on Page 5, left column, line 53, under "OTHER PUBLICATIONS", delete "Microencapulation," and insert -- Microencapsulation, --, therefor.

Title Page, Item (56), on Page 5, right column, line 66, under "OTHER PUBLICATIONS", delete "Phtochemistry" and insert -- Phytochemistry --, therefor.

Title Page, Item (56), on Page 6, left column, line 12, under "OTHER PUBLICATIONS", delete "Implanation," and insert -- Implantation, --, therefor.

Title Page, Item (56), on Page 6, left column, line 29, under "OTHER PUBLICATIONS", delete "Uncaoted Calloon" and insert -- Uncoated Balloon --, therefor.

Title Page, Item (56), on Page 6, left column, line 52, under "OTHER PUBLICATIONS", delete "Preassure," and insert -- Pressure, --, therefor.

Signed and Sealed this
Nineteenth Day of March, 2013

Teresa Stanek Rea
*Acting Director of the United States Patent and Trademark Office*

CERTIFICATE OF CORRECTION (continued)
U.S. Pat. No. 8,257,305 B2

Title Page, Item (56), on Page 6, right column, line 16, under "OTHER PUBLICATIONS", delete "pacliTaxel" and insert -- paclitaxel --, therefor.

Title Page, Item (56), on Page 6, right column, line 22, under "OTHER PUBLICATIONS", delete "Artheriosklerosis," and insert -- Arteriosklerosis, --, therefor.

Title Page, Item (56), on Page 7, right column, line 62, under "OTHER PUBLICATIONS", delete "angiRplasty" and insert -- angioplasty --, therefor.

IN THE SPECIFICATION

In Column 6, Line 63, delete "HPLC" and insert -- HPLC. --, therefor.

In Column 6, Line 65, delete "300" and insert -- 300. --, therefor.

In Column 6, Line 67, delete "300" and insert -- 300. --, therefor.

In Column 7, Line 12, delete "+4.5 ul" and insert -- +4.5 μl --, therefor.

In Column 7, Line 39, delete "+100 ul" and insert -- +100 μl --, therefor.

IN THE CLAIMS

In Claim 3, Column 8, Lines 63-64, delete "wherein a balloon with preformed longitudinal folds is coated with the drug" and insert -- wherein the balloon further comprising preformed longitudinal folds is coated with the drug --, therefor.

In Claim 4, Column 8, Line 66, delete "wherein a balloon" and insert -- wherein the balloon --, therefor.

In Claim 5, Column 9, Lines 3-4, delete "wherein only the area covered by folds" and insert -- wherein only an area covered by folds --, therefor.

In Claim 9, Column 9, Line 17, delete "on the surface of the device." and insert -- on the smooth surface of the balloon. --, therefor.

In Claim 10, Column 9, Line 18, delete "wherein the dosage form" and insert -- wherein a dosage form --, therefor.

In Claim 11, Column 9, Line 25, delete "the surface of the device" and insert -- the smooth surface of the balloon --, therefor.

In Claim 14, Column 9, Lines 33-35, delete "is absorbed to particles of or applied to the surface of the device" and insert -- is adsorbed to particles of or applied to the smooth surface of the balloon --, therefor.

CERTIFICATE OF CORRECTION (continued)
U.S. Pat. No. 8,257,305 B2

IN THE CLAIMS

In Claim 17, Column 9, Line 46, delete "the surface of the device" and insert -- the smooth surface of the balloon --, therefor.

In Claim 18, Column 9, Line 51, delete "using the same" and insert -- using a same --, therefor.

In Claim 20, Column 9, Lines 57-59, delete "wherein a balloon folded ready for use is used as the drug carrier coated" and insert -- wherein the folded balloon is used as a drug carrier and is coated --, therefor.

In Claim 23, Column 9, Lines 66-67, delete "the completely coated device" and insert -- the coated balloon --, therefor.

In Claim 26, Column 10, Line 10, delete "wherein the balloon" and insert -- wherein a balloon --, therefor.

In Claim 28, Column 10, Lines 16-17, delete "according to claim 26, comprising in its finally folded state a balloon coated" and insert -- according to claim 26, comprising a balloon that, in its finally folded state, is coated --, therefor.

In Claim 32, Column 10, Lines 30-31, delete "wherein the dosage form" and insert -- wherein a dosage form --, therefor.

In Claim 39, Column 10, Lines 52-53, delete "drug is absorbed to a particle or applied to the surface of the device" and insert -- drug is adsorbed to a particle or applied to the smooth surface of the balloon --, therefor.

In Claim 42, Column 10, Line 61, delete "producing the coated balloon" and insert -- producing a balloon --, therefor.

In Claim 42, Column 10, Line 65, delete "surface of a folded balloon" and insert -- surface of the folded balloon --, therefor.

In Claim 43, Column 11, Line 3, delete "using the same" and insert -- using a same --, therefor.

In Claim 43, Column 11, Lines 1-2, delete "wherein the coating process" and insert -- wherein the application process --, therefor.

In Claim 45, Column 11, Lines 10-11, delete "used as the drug carrier" and insert -- used as a drug carrier --, therefor.

UNITED STATES PATENT AND TRADEMARK OFFICE
CERTIFICATE OF CORRECTION

| | |
|---|---|
| PATENT NO. | : 8,257,305 B2 |
| APPLICATION NO. | : 10/528577 |
| DATED | : September 4, 2012 |
| INVENTOR(S) | : Ulrich Speck et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 961 days.

Signed and Sealed this
Twenty-fourth Day of February, 2015

Michelle K. Lee
*Deputy Director of the United States Patent and Trademark Office*